(12) United States Patent
Razzaque et al.

(10) Patent No.: US 9,107,698 B2
(45) Date of Patent: *Aug. 18, 2015

(54) IMAGE ANNOTATION IN IMAGE-GUIDED MEDICAL PROCEDURES

(71) Applicant: InnerOptic Technology, Inc., Hillsborough, NC (US)

(72) Inventors: Sharif Razzaque, Chapel Hill, NC (US); Andrei State, Chapel Hill, NC (US)

(73) Assignee: InnerOptic Technology, Inc., Hillsborough, NC (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/047,628

(22) Filed: Oct. 7, 2013

(65) Prior Publication Data

US 2014/0094687 A1    Apr. 3, 2014

Related U.S. Application Data

(63) Continuation of application No. 13/014,596, filed on Jan. 26, 2011, now Pat. No. 8,554,307.

(60) Provisional application No. 61/322,991, filed on Apr. 12, 2010, provisional application No. 61/387,132, filed on Sep. 28, 2010.

(51) Int. Cl.
*A61B 5/05* (2006.01)
*A61B 19/00* (2006.01)
(Continued)

(52) U.S. Cl.
CPC .............. *A61B 19/5244* (2013.01); *A61B 5/748* (2013.01); *A61B 6/032* (2013.01);
(Continued)

(58) Field of Classification Search
CPC .................................................. A61B 19/5244

USPC ........................................... 600/424; 382/128
See application file for complete search history.

(56) References Cited

U.S. PATENT DOCUMENTS 3,556,079 A    1/1971    Omizo
4,058,114 A    11/1977    Soldner
(Continued)

FOREIGN PATENT DOCUMENTS

AU    7656896 A    5/1997
AU    9453898 A    4/1999
(Continued)

OTHER PUBLICATIONS

"3D Laparoscope Technology," http://www.inneroptic.com/tech_3DL.htm, copyright 2007 InnerOptic Technology, Inc. printed Sep. 19, 2007, 2 pages.
(Continued)

*Primary Examiner* — Rajeev Siripurapu
(74) *Attorney, Agent, or Firm* — Knobbe, Martens, Olson & Bear, LLP

(57) ABSTRACT

Presented herein are methods, systems, devices, and computer-readable media for image annotation in image-guided medical procedures. Some embodiments herein allow physicians or other operators to use one or more medical devices in order to define annotations in 3D space. These annotations may later be displayed to the physician or operator in 3D space in the position in which they were first drawn or otherwise generated. In some embodiments, the operator may use various available medical devices, such as needles, scalpels, or even a finger in order to define the annotation. Embodiments herein may allow an operator to more conveniently and efficiently annotate visualizable medical data.

16 Claims, 9 Drawing Sheets

(51) Int. Cl.
*A61B 6/00* (2006.01)
*A61B 8/00* (2006.01)
*A61B 8/08* (2006.01)
*A61B 5/00* (2006.01)
*A61B 6/03* (2006.01)
*A61B 8/12* (2006.01)
*A61B 18/14* (2006.01)
*A61B 17/00* (2006.01)

(52) U.S. Cl.
CPC .............. *A61B 6/4494* (2013.01); *A61B 6/466* (2013.01); *A61B 6/468* (2013.01); *A61B 6/5217* (2013.01); *A61B 6/5247* (2013.01); *A61B 8/12* (2013.01); *A61B 8/466* (2013.01); *A61B 8/468* (2013.01); *A61B 8/5223* (2013.01); *A61B 18/1477* (2013.01); *A61B 19/56* (2013.01); *A61B 8/483* (2013.01); *A61B 2017/00207* (2013.01); *A61B 2019/5248* (2013.01); *A61B 2019/5251* (2013.01); *A61B 2019/5255* (2013.01); *A61B 2019/5276* (2013.01)

(56) References Cited

U.S. PATENT DOCUMENTS

| | | |
|---|---|---|
| RE30,397 E | 9/1980 | King |
| 4,249,539 A | 2/1981 | Vilkomerson et al. |
| 4,294,544 A | 10/1981 | Altschuler et al. |
| 4,390,025 A | 6/1983 | Takemura et al. |
| 4,407,294 A | 10/1983 | Vilkomerso |
| 4,431,006 A | 2/1984 | Trimmer et al. |
| 4,567,896 A | 2/1986 | Barnea et al. |
| 4,583,538 A | 4/1986 | Onik et al. |
| 4,620,546 A | 11/1986 | Aida et al. |
| 4,671,292 A | 6/1987 | Matzuk |
| 4,839,836 A | 6/1989 | Fonsalas |
| 4,862,873 A | 9/1989 | Yajima et al. |
| 4,884,219 A | 11/1989 | Waldren |
| 4,899,756 A | 2/1990 | Sonek |
| 4,911,173 A | 3/1990 | Terwillige |
| 4,945,305 A | 7/1990 | Blood |
| 5,076,279 A | 12/1991 | Arenson et al. |
| 5,078,140 A | 1/1992 | Kwoh |
| 5,078,142 A | 1/1992 | Siczek et al. |
| 5,095,910 A | 3/1992 | Powers |
| 5,109,276 A | 4/1992 | Nudelman et al. |
| 5,158,088 A | 10/1992 | Nelson et al. |
| 5,161,536 A | 11/1992 | Vilkomerson et al. |
| 5,193,120 A | 3/1993 | Gamache et al. |
| 5,209,235 A | 5/1993 | Brisken et al. |
| 5,249,581 A | 10/1993 | Horbal et al. |
| 5,251,127 A | 10/1993 | Raab |
| 5,261,404 A | 11/1993 | Mick et al. |
| 5,265,610 A | 11/1993 | Darrow et al. |
| 5,271,400 A | 12/1993 | Dumoulin et al. |
| 5,307,153 A | 4/1994 | Maruyama et al. |
| 5,309,913 A | 5/1994 | Kormos et al. |
| 5,323,002 A | 6/1994 | Sampsell et al. |
| 5,371,543 A | 12/1994 | Anderson |
| 5,383,454 A | 1/1995 | Bucholz |
| 5,394,875 A | 3/1995 | Lewis et al. |
| 5,411,026 A | 5/1995 | Carol |
| 5,433,198 A | 7/1995 | Desai |
| 5,433,739 A | 7/1995 | Sluijter |
| 5,443,489 A | 8/1995 | Ben-Haim |
| 5,446,798 A | 8/1995 | Morita et al. |
| 5,447,154 A | 9/1995 | Cinquin et al. |
| 5,452,024 A | 9/1995 | Sampsell |
| 5,457,493 A | 10/1995 | Leddy et al. |
| 5,474,073 A | 12/1995 | Schwartz et al. |
| 5,476,096 A | 12/1995 | Olstad et al. |
| 5,483,961 A | 1/1996 | Kelly et al. |
| 5,488,431 A | 1/1996 | Gove et al. |
| 5,489,952 A | 2/1996 | Gove et al. |
| 5,491,510 A | 2/1996 | Gove |
| 5,494,039 A | 2/1996 | Onik et al. |
| 5,503,152 A | 4/1996 | Oakley et al. |
| 5,505,204 A | 4/1996 | Picot et al. |
| 5,515,856 A | 5/1996 | Olstad et al. |
| 5,517,990 A | 5/1996 | Kalfas et al. |
| 5,526,051 A | 6/1996 | Gove et al. |
| 5,526,812 A | 6/1996 | Dumoulin et al. |
| 5,529,070 A | 6/1996 | Augustine et al. |
| 5,531,227 A | 7/1996 | Schneider |
| 5,532,997 A | 7/1996 | Pauli |
| 5,541,723 A | 7/1996 | Tanaka |
| 5,558,091 A | 9/1996 | Acker et al. |
| 5,568,811 A | 10/1996 | Olstad |
| 5,570,135 A | 10/1996 | Gove et al. |
| 5,579,026 A | 11/1996 | Tabata |
| 5,581,271 A | 12/1996 | Kraemer |
| 5,588,948 A | 12/1996 | Takahashi et al. |
| 5,608,468 A | 3/1997 | Gove et al. |
| 5,608,849 A | 3/1997 | King, Jr. |
| 5,611,345 A | 3/1997 | Hibbeln |
| 5,611,353 A | 3/1997 | Dance et al. |
| 5,612,753 A | 3/1997 | Poradish et al. |
| 5,625,408 A | 4/1997 | Matsugu et al. |
| 5,628,327 A | 5/1997 | Unger et al. |
| 5,629,794 A | 5/1997 | Magel et al. |
| 5,630,027 A | 5/1997 | Venkateswar et al. |
| 5,647,361 A | 7/1997 | Damadian |
| 5,647,373 A | 7/1997 | Paltieli et al. |
| 5,660,185 A | 8/1997 | Shmulewitz et al. |
| 5,662,111 A | 9/1997 | Cosman |
| 5,699,444 A | 12/1997 | Palm |
| 5,701,898 A | 12/1997 | Adam et al. |
| 5,701,900 A | 12/1997 | Shehada et al. |
| 5,726,670 A | 3/1998 | Tabata et al. |
| 5,728,044 A | 3/1998 | Shan |
| 5,758,650 A | 6/1998 | Miller et al. |
| 5,766,135 A | 6/1998 | Terwilliger |
| 5,784,098 A | 7/1998 | Shoji et al. |
| 5,792,147 A | 8/1998 | Evans et al. |
| 5,793,701 A | 8/1998 | Wright et al. |
| 5,797,849 A | 8/1998 | Vesely et al. |
| 5,807,395 A | 9/1998 | Mulier et al. |
| 5,810,008 A | 9/1998 | Dekel et al. |
| 5,817,022 A | 10/1998 | Vesely |
| 5,820,554 A | 10/1998 | Davis et al. |
| 5,820,561 A | 10/1998 | Olstad et al. |
| 5,829,439 A | 11/1998 | Yokosawa et al. |
| 5,829,444 A | 11/1998 | Ferre et al. |
| 5,851,183 A | 12/1998 | Bodiolz |
| 5,870,136 A | 2/1999 | Fuchs et al. |
| 5,891,034 A | 4/1999 | Bucholz |
| 5,920,395 A | 7/1999 | Schulz |
| 5,961,527 A | 10/1999 | Whitmore, III et al. |
| 5,967,980 A | 10/1999 | Ferre et al. |
| 5,991,085 A | 11/1999 | Rallison et al. |
| 6,016,439 A | 1/2000 | Acker |
| 6,019,724 A | 2/2000 | Gronningsaeter et al. |
| 6,048,312 A | 4/2000 | Ishrak et al. |
| 6,064,749 A | 5/2000 | Hirota et al. |
| 6,091,546 A | 7/2000 | Spitzer |
| 6,095,982 A | 8/2000 | Richards-Kortum et al. |
| 6,099,471 A | 8/2000 | Torp et al. |
| 6,108,130 A | 8/2000 | Raj |
| 6,122,538 A | 9/2000 | Sliwa, Jr. et al. |
| 6,122,541 A | 9/2000 | Cosman et al. |
| 6,160,666 A | 12/2000 | Rallison et al. |
| 6,167,296 A | 12/2000 | Shahidi |
| 6,181,371 B1 | 1/2001 | Maguire, Jr. |
| RE37,088 E | 3/2001 | Olstad et al. |
| 6,216,029 B1 | 4/2001 | Paltieli |
| 6,241,725 B1 | 6/2001 | Cosman |
| 6,245,017 B1 | 6/2001 | Hashimoto et al. |
| 6,246,898 B1 | 6/2001 | Vesely et al. |
| 6,248,101 B1 | 6/2001 | Witmore, III et al. |
| 6,261,234 B1 | 7/2001 | Lin |
| 6,341,016 B1 | 1/2002 | Malione |
| 6,348,058 B1 | 2/2002 | Melken et al. |

(56) References Cited

U.S. PATENT DOCUMENTS

| | | |
|---|---|---|
| 6,350,238 B1 | 2/2002 | Olstad et al. |
| 6,352,507 B1 | 3/2002 | Torp et al. |
| 6,379,302 B1 | 4/2002 | Kessman et al. |
| 6,385,475 B1 | 5/2002 | Cinquin et al. |
| 6,442,417 B1 | 8/2002 | Shahidi et al. |
| 6,447,450 B1 | 9/2002 | Olstad |
| 6,456,868 B2 | 9/2002 | Saito et al. |
| 6,470,207 B1 | 10/2002 | Simon et al. |
| 6,471,366 B1 | 10/2002 | Hughson et al. |
| 6,477,400 B1 | 11/2002 | Barrick |
| 6,478,793 B1 | 11/2002 | Cosman et al. |
| 6,503,195 B1 | 1/2003 | Keller et al. |
| 6,511,418 B2 | 1/2003 | Shahidi et al. |
| 6,517,485 B2 | 2/2003 | Torp et al. |
| 6,518,939 B1 | 2/2003 | Kikuchi |
| 6,527,443 B1 | 3/2003 | Vilsmeier et al. |
| 6,529,758 B2 | 3/2003 | Shahidi |
| 6,537,217 B1 | 3/2003 | Bjærum et al. |
| 6,545,706 B1 | 4/2003 | Edwards et al. |
| 6,546,279 B1 | 4/2003 | Bova et al. |
| 6,551,325 B2 | 4/2003 | Neubauer et al. |
| 6,570,566 B1 | 5/2003 | Yoshigahara |
| 6,575,969 B1 | 6/2003 | Rittman, III et al. |
| 6,579,240 B2 | 6/2003 | Bjaerum et al. |
| 6,587,711 B1 | 7/2003 | Alfano et al. |
| 6,591,130 B2 | 7/2003 | Shahidi |
| 6,592,522 B2 | 7/2003 | Bjaerum et al. |
| 6,594,517 B1 | 7/2003 | Nevo |
| 6,597,818 B2 | 7/2003 | Kumar et al. |
| 6,604,404 B2 | 8/2003 | Paltieli et al. |
| 6,616,610 B2 | 9/2003 | Steininger et al. |
| 6,626,832 B1 | 9/2003 | Paltieli et al. |
| 6,652,462 B2 | 11/2003 | Bjaerum et al. |
| 6,669,635 B2 | 12/2003 | Kessman et al. |
| 6,676,599 B2 | 1/2004 | Torp et al. |
| 6,689,067 B2 | 2/2004 | Sauer et al. |
| 6,695,786 B2 | 2/2004 | Wang et al. |
| 6,711,429 B1 | 3/2004 | Gilboa et al. |
| 6,725,082 B2 | 4/2004 | Sati et al. |
| 6,733,458 B1 | 5/2004 | Steins et al. |
| 6,764,449 B2 | 7/2004 | Lee et al. |
| 6,766,184 B2 | 7/2004 | Utzinger et al. |
| 6,768,496 B2 | 7/2004 | Bieger et al. |
| 6,775,404 B1 | 8/2004 | Pagoulatos et al. |
| 6,782,287 B2 | 8/2004 | Grzeszczuk et al. |
| 6,783,524 B2 | 8/2004 | Anderson et al. |
| 6,827,723 B2 | 12/2004 | Carson |
| 6,863,655 B2 | 3/2005 | Bjaerum et al. |
| 6,873,867 B2 | 3/2005 | Vilsmeier |
| 6,875,179 B2 | 4/2005 | Ferguson et al. |
| 6,881,214 B2 | 4/2005 | Cosman et al. |
| 6,895,268 B1 | 5/2005 | Rahn et al. |
| 6,915,150 B2 | 7/2005 | Cinquin et al. |
| 6,917,827 B2 | 7/2005 | Kienzle, III |
| 6,923,817 B2 | 8/2005 | Carson et al. |
| 6,936,048 B2 | 8/2005 | Hurst |
| 6,947,783 B2 | 9/2005 | Immerz |
| 6,968,224 B2 | 11/2005 | Kessman et al. |
| 6,978,167 B2 | 12/2005 | Dekel et al. |
| 7,008,373 B2 | 3/2006 | Stoianovici et al. |
| 7,033,360 B2 | 4/2006 | Cinquin et al. |
| 7,072,707 B2 | 7/2006 | Galloway, Jr. et al. |
| 7,077,807 B2 | 7/2006 | Torp et al. |
| 7,093,012 B2 | 8/2006 | Olstad et al. |
| 7,110,013 B2 | 9/2006 | Ebersole et al. |
| 7,171,255 B2 | 1/2007 | Holupka et al. |
| 7,209,776 B2 | 4/2007 | Leitner |
| 7,245,746 B2 | 7/2007 | Bjaerum et al. |
| 7,248,232 B1 | 7/2007 | Yamazaki et al. |
| 7,261,694 B2 | 8/2007 | Torp et al. |
| 7,313,430 B2 | 12/2007 | Urquhart et al. |
| 7,331,932 B2 | 2/2008 | Leitner |
| 7,351,205 B2 | 4/2008 | Szczech et al. |
| 7,379,769 B2 | 5/2008 | Piron et al. |
| 7,385,708 B2 | 6/2008 | Ackerman et al. |
| 7,392,076 B2 | 6/2008 | Moctezuma de la Barrera |
| 7,398,116 B2 | 7/2008 | Edwards |
| 7,466,303 B2 | 12/2008 | Yi et al. |
| 7,480,533 B2 | 1/2009 | Cosman et al. |
| 7,505,809 B2 | 3/2009 | Strommer et al. |
| 7,588,541 B2 | 9/2009 | Floyd et al. |
| 7,652,259 B2 | 1/2010 | Kimchy et al. |
| 7,662,128 B2 | 2/2010 | Salcudean et al. |
| 7,678,052 B2 | 3/2010 | Torp et al. |
| 7,728,868 B2 | 6/2010 | Razzaque et al. |
| 7,797,032 B2 | 9/2010 | Martinelli et al. |
| 7,798,965 B2 | 9/2010 | Torp et al. |
| 7,833,168 B2 | 11/2010 | Taylor et al. |
| 7,833,221 B2 | 11/2010 | Voegele et al. |
| 7,846,103 B2 | 12/2010 | Cannon, Jr. et al. |
| 7,876,942 B2 | 1/2011 | Gilboa |
| 7,889,905 B2 | 2/2011 | Higgins et al. |
| 7,901,357 B2 | 3/2011 | Bova et al. |
| 7,912,849 B2 | 3/2011 | Ohrn et al. |
| 7,920,909 B2 | 4/2011 | Lyon et al. |
| 7,962,193 B2 | 6/2011 | Edwards et al. |
| 7,976,469 B2 | 7/2011 | Bonde et al. |
| 8,023,712 B2 | 9/2011 | Ikuma et al. |
| 8,038,631 B1 | 10/2011 | Sanghvi et al. |
| 8,041,413 B2 | 10/2011 | Barbagli et al. |
| 8,050,736 B2 | 11/2011 | Piron et al. |
| 8,052,636 B2 | 11/2011 | Moll et al. |
| 8,066,644 B2 | 11/2011 | Sarkar et al. |
| 8,073,528 B2 | 12/2011 | Zhao et al. |
| 8,086,298 B2 | 12/2011 | Whitmore, III et al. |
| 8,135,669 B2 | 3/2012 | Olstad et al. |
| 8,137,281 B2 | 3/2012 | Huang et al. |
| 8,147,408 B2 | 4/2012 | Bunce et al. |
| 8,152,724 B2 | 4/2012 | Ridley et al. |
| 8,167,805 B2 | 5/2012 | Emery et al. |
| 8,216,149 B2 | 7/2012 | Oonuki et al. |
| 8,221,322 B2 | 7/2012 | Wang et al. |
| 8,228,028 B2 | 7/2012 | Schneider |
| 8,257,264 B2 | 9/2012 | Park et al. |
| 8,296,797 B2 | 10/2012 | Olstad et al. |
| 8,340,379 B2 | 12/2012 | Razzaque et al. |
| 8,350,902 B2 | 1/2013 | Razzaque et al. |
| 8,482,606 B2 | 7/2013 | Razzaque et al. |
| 8,554,307 B2 | 10/2013 | Razzaque et al. |
| 8,641,621 B2 | 2/2014 | Razzaque et al. |
| 8,670,816 B2 | 3/2014 | Green et al. |
| 8,831,310 B2 | 9/2014 | Razzaque et al. |
| 2001/0007919 A1 | 7/2001 | Shahidi |
| 2001/0016804 A1 | 8/2001 | Cunningham et al. |
| 2001/0045979 A1 | 11/2001 | Matsumoto et al. |
| 2002/0010384 A1 | 1/2002 | Shahidi et al. |
| 2002/0032772 A1 | 3/2002 | Olstad et al. |
| 2002/0049375 A1 | 4/2002 | Strommer et al. |
| 2002/0077540 A1 | 6/2002 | Kienzie, III |
| 2002/0077543 A1 | 6/2002 | Grzeszczuk et al. |
| 2002/0105484 A1 | 8/2002 | Navab et al. |
| 2002/0135673 A1 | 9/2002 | Favalora et al. |
| 2002/0138008 A1 | 9/2002 | Tsujita et al. |
| 2002/0140814 A1 | 10/2002 | Cohen-Solal et al. |
| 2002/0156375 A1 | 10/2002 | Kessmam et al. |
| 2002/0198451 A1 | 12/2002 | Carson |
| 2003/0040743 A1 | 2/2003 | Cosman et al. |
| 2003/0073901 A1 | 4/2003 | Simon et al. |
| 2003/0135119 A1 | 7/2003 | Lee et al. |
| 2003/0163142 A1 | 8/2003 | Paltieli et al. |
| 2003/0164172 A1 | 9/2003 | Chumas et al. |
| 2003/0231789 A1 | 12/2003 | Willis et al. |
| 2004/0034313 A1 | 2/2004 | Leitner |
| 2004/0078036 A1 | 4/2004 | Keidar |
| 2004/0095507 A1 | 5/2004 | Bishop et al. |
| 2004/0116810 A1 | 6/2004 | Olstad |
| 2004/0147920 A1 | 7/2004 | Keidar |
| 2004/0152970 A1 | 8/2004 | Hunter et al. |
| 2004/0181144 A1 | 9/2004 | Cinquin et al. |
| 2004/0215071 A1 | 10/2004 | Frank et al. |
| 2004/0238732 A1 | 12/2004 | State et al. |
| 2004/0243146 A1 | 12/2004 | Chesbrough et al. |
| 2004/0243148 A1 | 12/2004 | Wasielewski |
| 2004/0249281 A1 | 12/2004 | Olstad |

(56) References Cited

U.S. PATENT DOCUMENTS

| | | |
|---|---|---|
| 2004/0249282 A1 | 12/2004 | Olstad |
| 2004/0254454 A1 | 12/2004 | Kockro |
| 2005/0010098 A1 | 1/2005 | Frigstad et al. |
| 2005/0085717 A1 | 4/2005 | Shahidi |
| 2005/0085718 A1 | 4/2005 | Shahidi |
| 2005/0090742 A1 | 4/2005 | Mine et al. |
| 2005/0111733 A1 | 5/2005 | Fors et al. |
| 2005/0159641 A1 | 7/2005 | Kanai |
| 2005/0182316 A1 | 8/2005 | Burdette et al. |
| 2005/0192564 A1 | 9/2005 | Cosman et al. |
| 2005/0219552 A1 | 10/2005 | Ackerman et al. |
| 2005/0222574 A1 | 10/2005 | Giordano et al. |
| 2005/0251148 A1 | 11/2005 | Friedrich |
| 2006/0004275 A1 | 1/2006 | Vija et al. |
| 2006/0020204 A1 | 1/2006 | Serra et al. |
| 2006/0036162 A1 | 2/2006 | Shahidi et al. |
| 2006/0052792 A1 | 3/2006 | Boettiger et al. |
| 2006/0058609 A1 | 3/2006 | Olstad |
| 2006/0058610 A1 | 3/2006 | Olstad |
| 2006/0058674 A1 | 3/2006 | Olstad |
| 2006/0058675 A1 | 3/2006 | Olstad |
| 2006/0100505 A1 | 5/2006 | Viswanathan |
| 2006/0122495 A1 | 6/2006 | Kienzle |
| 2006/0184040 A1 | 8/2006 | Keller et al. |
| 2006/0193504 A1 | 8/2006 | Salgo et al. |
| 2006/0229594 A1 | 10/2006 | Francischelli et al. |
| 2006/0235290 A1 | 10/2006 | Gabriel et al. |
| 2006/0235538 A1 | 10/2006 | Rochetin et al. |
| 2006/0241450 A1 | 10/2006 | Da Silva et al. |
| 2006/0253030 A1 | 11/2006 | Altmann et al. |
| 2006/0253032 A1 | 11/2006 | Altmann et al. |
| 2006/0271056 A1 | 11/2006 | Terrill-Grisoni et al. |
| 2006/0282023 A1 | 12/2006 | Leitner |
| 2006/0293643 A1 | 12/2006 | Wallace et al. |
| 2007/0016035 A1 | 1/2007 | Hashimoto |
| 2007/0032906 A1 | 2/2007 | Sutherland et al. |
| 2007/0073155 A1 | 3/2007 | Park et al. |
| 2007/0073455 A1 | 3/2007 | Park et al. |
| 2007/0078346 A1 | 4/2007 | Park et al. |
| 2007/0167699 A1 | 7/2007 | Lathuiliere et al. |
| 2007/0167701 A1 | 7/2007 | Sherman |
| 2007/0167705 A1 | 7/2007 | Chiang et al. |
| 2007/0167771 A1 | 7/2007 | Olstad |
| 2007/0167801 A1 | 7/2007 | Webler et al. |
| 2007/0225553 A1 | 9/2007 | Shahidi |
| 2007/0239281 A1 | 10/2007 | Gotte et al. |
| 2007/0244488 A1 | 10/2007 | Metzger et al. |
| 2007/0255136 A1 | 11/2007 | Kristofferson et al. |
| 2007/0270718 A1 | 11/2007 | Rochetin et al. |
| 2007/0276234 A1 | 11/2007 | Shahidi |
| 2008/0004481 A1 | 1/2008 | Bax et al. |
| 2008/0004516 A1 | 1/2008 | DiSilvestro et al. |
| 2008/0030578 A1 | 2/2008 | Razzaque et al. |
| 2008/0039723 A1 | 2/2008 | Suri et al. |
| 2008/0051910 A1 | 2/2008 | Kammerzell et al. |
| 2008/0091106 A1 | 4/2008 | Kim et al. |
| 2008/0114235 A1 | 5/2008 | Unal et al. |
| 2008/0161824 A1 | 7/2008 | McMillen |
| 2008/0200794 A1 | 8/2008 | Teichman et al. |
| 2008/0208031 A1 | 8/2008 | Kurpad et al. |
| 2008/0208081 A1 | 8/2008 | Murphy et al. |
| 2008/0214932 A1 | 9/2008 | Mollard et al. |
| 2008/0232679 A1 | 9/2008 | Hahn et al. |
| 2008/0287794 A1 | 11/2008 | Li et al. |
| 2008/0287805 A1 | 11/2008 | Li |
| 2008/0287837 A1 | 11/2008 | Makin et al. |
| 2009/0024030 A1 | 1/2009 | Lachaine et al. |
| 2009/0118724 A1 | 5/2009 | Zvuloni et al. |
| 2009/0137907 A1 | 5/2009 | Takimoto et al. |
| 2009/0226069 A1 | 9/2009 | Razzaque et al. |
| 2009/0234369 A1 | 9/2009 | Bax et al. |
| 2009/0312629 A1 | 12/2009 | Razzaque et al. |
| 2010/0045783 A1 | 2/2010 | State et al. |
| 2010/0198045 A1 | 8/2010 | Razzaque et al. |
| 2010/0208963 A1 | 8/2010 | Kruecker et al. |
| 2010/0268067 A1 | 10/2010 | Razzaque et al. |
| 2010/0268072 A1 | 10/2010 | Hall et al. |
| 2010/0268085 A1 | 10/2010 | Kruecker et al. |
| 2010/0305448 A1 | 12/2010 | Dagonnau et al. |
| 2010/0312121 A1 | 12/2010 | Guan |
| 2010/0331252 A1 | 12/2010 | Clements et al. |
| 2011/0043612 A1 | 2/2011 | Keller et al. |
| 2011/0046483 A1 | 2/2011 | Fuchs et al. |
| 2011/0046486 A1 | 2/2011 | Shin et al. |
| 2011/0057930 A1 | 3/2011 | Keller |
| 2011/0082351 A1 | 4/2011 | Razzaque et al. |
| 2011/0130641 A1 | 6/2011 | Razzaque et al. |
| 2011/0137156 A1 | 6/2011 | Razzaque et al. |
| 2011/0201915 A1 | 8/2011 | Gogin et al. |
| 2011/0201976 A1 | 8/2011 | Sanghvi et al. |
| 2011/0230351 A1 | 9/2011 | Fischer et al. |
| 2011/0237947 A1 | 9/2011 | Boctor et al. |
| 2011/0238043 A1 | 9/2011 | Kleven |
| 2011/0251483 A1 | 10/2011 | Razzaque et al. |
| 2011/0274324 A1 | 11/2011 | Clements et al. |
| 2011/0282188 A1 | 11/2011 | Burnside et al. |
| 2011/0288412 A1 | 11/2011 | Deckman et al. |
| 2011/0295108 A1 | 12/2011 | Cox et al. |
| 2011/0301451 A1 | 12/2011 | Rohling |
| 2012/0035473 A1 | 2/2012 | Sanghvi et al. |
| 2012/0059260 A1 | 3/2012 | Robinson |
| 2012/0071759 A1 | 3/2012 | Hagy et al. |
| 2012/0078094 A1 | 3/2012 | Nishina et al. |
| 2012/0101370 A1 | 4/2012 | Razzaque et al. |
| 2012/0108955 A1 | 5/2012 | Razzaque et al. |
| 2012/0143029 A1 | 6/2012 | Silverstein et al. |
| 2012/0143055 A1 | 6/2012 | Cheng et al. |
| 2012/0165679 A1 | 6/2012 | Orome et al. |
| 2012/0259210 A1 | 10/2012 | Harhen et al. |
| 2013/0030286 A1 | 1/2013 | Alouani et al. |
| 2013/0044930 A1 | 2/2013 | Li et al. |
| 2013/0079770 A1 | 3/2013 | Kyle, Jr. et al. |
| 2013/0129175 A1 | 5/2013 | Razzaque |
| 2013/0132374 A1 | 5/2013 | Olstad et al. |
| 2013/0151533 A1 | 6/2013 | Udupa et al. |
| 2013/0178745 A1 | 7/2013 | Kyle et al. |
| 2014/0016848 A1 | 1/2014 | Razzaque et al. |
| 2014/0078138 A1 | 3/2014 | Martin et al. |
| 2014/0180074 A1 | 6/2014 | Green |

FOREIGN PATENT DOCUMENTS

| | | |
|---|---|---|
| AU | 1719601 A | 6/2001 |
| AU | 9036301 A | 3/2002 |
| AU | 2003297225 A1 | 7/2004 |
| AU | 2001290363 B2 | 2/2006 |
| BR | 0113882 A | 7/2003 |
| CA | 2420382 C | 4/2011 |
| DE | 60126798 T2 | 10/2007 |
| EP | 0 427 358 | 5/1991 |
| EP | 1955284 | 8/2008 |
| JP | S63-290550 A | 11/1988 |
| JP | H07-116164 A | 5/1995 |
| JP | 2005-058584 | 3/2005 |
| JP | 2005-323669 | 11/2005 |
| JP | 2009-517177 | 4/2009 |
| WO | WO 96/05768 | 2/1996 |
| WO | WO 97/15249 | 5/1997 |
| WO | WO 97/17014 | 5/1997 |
| WO | WO 99/26534 | 6/1999 |
| WO | WO 01/39683 | 6/2001 |
| WO | WO 03/032837 | 4/2003 |
| WO | WO 03/034705 | 4/2003 |
| WO | PCT/US2003/17987 | 12/2003 |
| WO | WO 03/105289 | 12/2003 |
| WO | WO 2005/010711 | 2/2005 |
| WO | WO 2007/019216 | 2/2007 |
| WO | WO 2007/067323 A2 | 6/2007 |
| WO | WO 2007/067323 A3 | 9/2007 |
| WO | WO 2008/017051 | 2/2008 |
| WO | WO 2009/063423 | 5/2009 |
| WO | WO 2009/094646 | 7/2009 |
| WO | WO 2010/057315 | 5/2010 |
| WO | WO 2010/096419 | 8/2010 |

(56) References Cited

FOREIGN PATENT DOCUMENTS

| WO | WO 2011/014687 | 2/2011 |
|----|----------------|--------|
| WO | WO 2012/169990 | 12/2012 |
| WO | WO 2013/116240 | 8/2013 |

OTHER PUBLICATIONS

"Cancer Facts & Figures 2004," www.cancer.org/downloads/STT/CAFF_finalPWSecured.pdf, copyright 2004 American Cancer Society, Inc., printed Sep. 19, 2007, 60 pages.
"David Laserscanner <-Latest News <-Institute for Robotics and Process Control <-Te . . . ," http://www/rob.cs.tu-bs.de/en/news/david, printed Sep. 19, 2007, 1 page.
"Laser scanned 3d model Final" video, still image of video attached, http://www.youtube.com/watch?v=DaLglgmoUf8, copyright 2007 YouTube, LLC, printed Sep. 19, 2007, 2 pages.
"Olympus Endoscopic Ultrasound System," www.olympusamerica.com/msg_section/download_brochures/135_b_gfum130.pdf, printed Sep. 20, 2007, 20 pages.
"Point Grey Research Inc.—Imaging Products—Triclops SDK Samples," http://www.ptgrey.com/products/triclopsSDK/samples.asp, copyright 2007 Point Grey Research Inc., printed Sep. 19, 2007, 1 page.
"Robbins, Mike—Computer Vision Research—Stereo Depth Perception," http://www.compumike.com/vision/stereodepth.php, copyright 2007 Michael F. Robbins, printed Sep. 19, 2007, 3 pages.
"RUE, Registered Ultrasound-Endoscope," copyright 2007 InnerOptic Technology, Inc., 2 pages.
Advertisement, "Inspeck 3DC 3D Capturor," Inspeck 3DC 3D Capturor (www.inspeck.com), 1998.
Advertisement, "Virtual 3D High Speed Non-Contact Surface Perception," Virtual 3-D Technologies Corporation (www.virtual3dtech.com)., Dec. 21, 1998.
Advertisements, "Virtuoso," Visual Interface, Inc. (www.visint.com), Dec. 21, 1998.
Akka, "Automatic Software Control of Display Parameters for Stereoscopic Graphics Images," SPIE vol. 1669: Stereoscopic Displays and Applications III, pp. 31-38 (1992).
Ali et al., "Near Infrared Spectroscopy and Imaging to Probe Differences in Water Content in Normal and Cancer Human Prostate Tissues," Technology in Cancer Research & Treatment; Oct. 2004; 3(5):491-497; Adenine Press.
Aylward et al., Analysis of the Parameter Space of a Metric for Registering 3D Vascular Images, in W. Niessen and M. Viergever (Eds.): MICCAI 2001, LNCS 2208, pp. 932-939, 2001.
Aylward et al., Registration and Analysis of Vascular Images, International Journal of Computer Vision 55(2/3), 123-138, 2003.
Aylward, et al., Intra-Operative 3D Ultrasound Augmentation, Proceedings of the IEEE International Symposium on Biomedical Imaging, Washington, Jul. 2002.
Azuma, "A Survey of Augmented Reality," Presence: Teleoperators and Virtual Environments 6, 4:1-48 (Aug. 1997).
Bajura, Michael et al.,, "Merging Virtual Objects with the Real World: Seeing Ultrasound Imagery within the Patient," Computer Graphics, Proceedings of SIGGRAPH 1992, vol. 26(2), pp. 203-210, available from www.cs.unc.edu/~fuchs/publications/MergVirtObjs92.pdf, printed Sep. 20, 2007, 8 pages.
Benavides et al., "Multispectral digital colposcopy for in vivo detection of cervical cancer," Optics Express; May 19, 2003; 11(1 0) Optical Society of America; USA.
Beraldin, J.A. et al., "Optimized Position Sensors for Flying-Spot Active Triangulation Systems," Proceedings of the Fourth International Conference on a 3-D Digital Imaging and Modeling (3DIM), Banff, Alberta, Canada, Oct. 6-10, 2003, pp. 334-341, NRC 47083, copyright 2003 National Research Council of Canada, http://iit-iti.nrc-cnrc.gc.ca/iit-publications-iti/docs/NRC-47083.pdf, printed Sep. 19, 2007, 9 pages.
Billinghurst, M. et al., Research Directions in Handheld AR; Int. J. of Virtual Reality 5(2),51-58 (2006).
Bishop, Azuma et al., "Improving Static and Dynamic Registration in an Optical See-Through HMD," Paper Presented at SIGGRAPH '94 Annual Conference in Orlando, FL (1994).
Blais, F., "Review of 20 Years of Range Sensor Development," Journal of Electronic Imaging, 13(1): 231-240, Jan. 2004, NRC 46531, copyright 2004 National Research Council of Canada, http://iit-iti.nrc-cnrc.gc.ca/iit-publications-iti/docs/NRC-46531.pdf, printed Sep. 19, 2007, 14 pages.
Bouguet, Jean-Yves, "Camera Calibration Toolbox for Matlab," www.vision.caltech.edu/bouguetj/calib_doc, printed Sep. 20, 2007, 5 pages.
Buxton et al.; "Colposcopically directed punch biopsy: a potentially misleading investigation," British Journal of Obstetrics and Gynecology; Dec. 1991; 98:1273-1276.
Caines, Judy S. et al. Stereotaxic Needle Core Biopsy of Breast Lesions Using a Regular Mammographic Table with an Adaptable Stereotaxic Device, American Journal of Roentgenology, vol. 163, No. 2, Aug. 1994, pp. 317-321. Downloaded from www.ajrorline.org on Jul. 10, 2013.
Cancer Prevention & Early Detection Facts & Figures 2004; National Center for Tobacco-Free Kids; 2004; American Cancer Society; USA.
Cantor et al., "Cost-Effectiveness Analysis of Diagnosis and Management of Cervical Squamous Intraepithelial Lesions," Diagnostic Strategies for SILs; Feb. 1998; 91(2):270-277.
Catalano et al. "Multiphase helical CT findings after percutaneous ablation procedures for hepatocellular carcinoma." Abdom. Imaging, 25(6),2000, pp. 607-614.
Chiriboga et al., "Infrared Spectroscopy of Human Tissue. IV. Detection of Dysplastic and Neoplastic Changes of Human Cervical Tissue Via Infrared Microscopy," Cellular and Molecular Biology; 1998; 44(1): 219-229.
Crawford, David E. et al., "Computer Modeling of Prostate Biopsy: Tumor Size and Location—Not Clinical Significance—Determine Cancer Detection," Journal of Urology, Apr. 1998, vol. 159(4), pp. 1260-1264, 5 pages.
Deering, Michael "High Resolution Virtual Reality." Proceedings of SIGGRAPH '92, Computer Graphics, 26(2), 1992, pp. 195-202.
Depiero et al., "3-D Computer Vision Using Structured Light: Design, Calibration and Implementation Issues," The University of Tennessee, pp. 1-46, (1996).
Dodd, G.D. et al. "Minimally invasive treatment of malignant hepatic tumors: at the threshold of a major breakthrough." Radiographies 20(1),2000, pp. 9-27.
Drascic et al., "Perceptual Issues in Augmented Reality," SPIE vol. 2653: Stereoscopic Displays and Virtual Reality Systems III, pp. 123-134 (Feb. 1996).
Dumoulin, C.L. et al, Real-Time Position Monitoring of Invasive Devices Using Magnetic Resonance, Magnetic Resonance in Medicine, vol. 29, Issue 3, Mar. 1993, pp. 411-415.
Fahey et al., "Meta-analysis of Pap Test Accuracy; American Journal of Epidemiology," 1995 141(7):680-689; The John Hopkins University School of Hygiene and Public Health; USA.
Foxlin et al., "An Inertial Head-Orientation Tracker with Automatic Drift Compensation for Use with HMD's," Proceedings of the 1994 Virtual Reality Software and Technology Conference, Aug. 23-26, 1994, Singapore, pp. 159-173 (1994).
Fronheiser et al., Real-Time 3D Color Doppler for Guidance of Vibrating Interventional Devices, IEEE Ultrasonics Symposium, pp. 149-152 (2004).
Fuchs, Henry et al. "Augmented Reality Visualization for Laparoscopic Surgery," Proceedings of Medical Image Computing and Computer-Assisted Intervention (MICCAI) 1998, pp. 934-943, available from www.cs.unc.edu/~fuchs/publications/AugRealVis_LaparoSurg98.pdf, printed Sep. 20, 2007, 10 pages.
Fuchs, et al.: "Virtual Environments Technology to Aid Needle Biopsies of the Breast," Health Care in the Information Age, Ch. 6, pp. 60-61, Presented in San Diego, Jan. 17-20, 1996, published by IOS Press and Ohmsha Feb. 1996.

(56) References Cited

OTHER PUBLICATIONS

Garrett, William F. et al., "Real-Time Incremental Visualization of Dynamic Ultrasound Volumes Using Parallel BSP Trees," Proceedings of IEEE Visualization 1996, pp. 235-240, available from www.cs.unc.edu/~andrei/pubs/1996_VIS_dualBSP_Mac.pdf, printed Sep. 20, 2007, 7 pages.

Georgakoudi et al., "Trimodal spectroscopy for the detection and characterization of cervical precancers in vivo," American Journal of Obstetrics and Gynecology; Mar. 2002; 186(3):374-382; USA.

Herline et al., Surface Registration for Use in Interactive, Image-Guided Liver Surgery, Computer Aided Surgery 5:11-17 (2000).

Holloway, R.; Registration Error Analysis for Augmented Reality; Presence: Teleoperators and Virtual Environments 6(4), 413-432 (1997).

Hornung et al., "Quantitative near-infrared spectroscopy of cervical dysplasia in vivo," Human Reproduction; 1999; 14(11):2908-2916; European Society of Human Reproduction and Embryology.

Howard, M.D., et al.: "An Electronic Device for Needle Placement during Sonographically Guided Percutaneous Intervention", Radiology 2001; 218:905-911.

InnerAim Brochure; 3D Visualization Software for Simpler, Safer, more Precise Aiming, Published no earlier than Apr. 1, 2010.

InVision System Brochure; A "GPS" for Real-Time 3D Needle Visualization & Guidance, Published no earlier than Mar. 1, 2008.

InVision User Manual; Professional Instructions for Use, Published no earlier than Dec. 1, 2008.

Jacobs, Marco C. et al., "Managing Latency in Complex Augmented Reality Systems," ACM SIGGRAPH Proceedings of the Symposium of Interactive 3D Graphics 1997, pp. 49-54, available from www.cs.unc.edu/~us/Latency//ManagingRelativeLatency.html, printed Sep. 20, 2007, 12 pages.

Jolesz, Ferenc A, M.D., et al. MRI-Guided Laser-Induced Interstitial Thermotherapy: Basic Principles, SPIE Institute on Laser-Induced Interstitial Thermotherapy (L1TT), Jun. 22-23, 1995, Berlin, Germany.

Kadi, A Majeed, et al., Design and Simulation of an Articulated Surgical Arm for Guidling Sterotactic Neurosurgery, SPIE vol. 1708 Applications of Artificial Intelligence X: Machine Vision and Robotics (1992). Downloaded from: http://proceedings.spiedigitallibrary.org/ on Jul. 11, 2013.

Kanbara et al., "A Stereoscopic Video See-through Augmented Reality System Based on Real-time Vision-Based Registration," Nara Institute of Science and Technology, pp. 1-8 (2000).

Kato, Amami, et al., A frameless, armless navigational system for computer-assisted neurosurgery, Journal of Neurosurgery, vol. 74, No. 5, May 1991, pp. 845-849.

Lass, Amir, "Assessment of Ovarian Reserve," Human Reproduction, 2004, vol. 19(3), pp. 467-469, available from http://humrep.oxfordjournals.orgcgi/reprint/19/3/467, printed Sep. 20, 2007, 3 pages.

Lee et al., "Modeling Real Objects Using Video See-Through Augmented Reality," Presence, 11(2):144-157 (Apr. 2002).

Leven et al., DaVinci Canvas: A Telerobotic Surgical System with Integrated, Robot-Assisted, Laparoscopic Ultrasound Capability, in J. Duncan and G. Gerig (Eds.): MICCAI 2005, LNCS 3749, pp. 811-818, 2005.

Levy, et al., An Internet-Connected, Patient Specific, Deformable Brain Atlas Integrated into a Surgical Navigation System, Journal of Digital Imaging, vol. 10, No. 3. Suppl. 1 (August), 1997: pp. 231-237.

Livingston, Mark A. et al., "Magnetic Tracker Calibration for Improved Augmented Reality Registration," Presence: Teleoperators and Virtual Environments, 1997, vol. 6(5), pp. 532-546, available from www.cs.unc.edu/~andrei/pubs/1997_Presence_calibr.pdf, printed Sep. 20, 2007, 14 pages.

Matsunaga et al., "The Effect of the Ratio Difference of Overlapped Areas of Stereoscopic Images on each Eye in a Teleoperalion," Stereoscopic Displays and Virtual Reality Systems VII, Proceedings of SPIE, 3957:236-243 (2000).

Meehan, Michael et al., "Effect of Latency on Presence in Stressful Virtual Environment," Proceedings of IEEE Virtual Reality 2003, pp. 141-148, available from http://www.cs.unc.edu/~eve/pubs.html, printed Sep. 20, 2007, 9 pages.

Milgram et al., "Adaptation Effects in Stereo due to Online Changes in Camera Configuration," SPIE vol. 1669-13, Stereoscopic Displays and Applications III, pp. 1-12 (1992).

Mtchell et al., "Colposcopy for the Diagnosis of Squamous Intraepithelial lesions: A metaanalysis," Obstetrics and Gynecology; Apr. 1998; 91(4):626-631.

Nakamoto et al., 3D Ultrasound System Using a Magneto-optic Hybrid Tracker for Augmented Reality Visualization in Laparoscopic Liver Surgery, in T. Dohi and R. Kikinis (Eds.): MICCAI 2002, LNCS 2489, pp. 148-155, 2002.

Nordstrom et al., "Identification of Cervical Intraepithelial Neoplasia (CIN) Using UV-Excited Fluorescence and Diffuse-Reflectance Tissue Spectroscopy," Lasers in Surgery and Medicine; 2001; 29; pp. 118-127; Wiley-Liss, Inc.

Ohbuchi et al. "An Incremental Volume Rendering Algorithm for Interactive 3D Ultrasound Imaging", UNC-CH Computer Science Technical Report TR91-003, (1991).

Ohbuchi et al., "Incremental Volume Reconstruction and Rendering for 3D Ultrasound Imaging," Visualization in Biomedical Computing, SPIE Proceedings, pp. 312-323, (Oct. 13, 1992).

Ohbuchi, "Incremental Acquisition and Visualization of 3D Ultrasound Images," Ph.D. Dissertation, UNC-CH Computer Science Technical Report TR95-023, (1993).

PCT, International Search Report and Written Opinion, re PCT Application No. PCT/US07/75122, mailing date Aug. 20, 2008.

PCT, International Preliminary Report on Patentability, re PCT Application No. PCT/US07/75122, mailing date Mar. 3, 2009.

PCT, International Search Report and Written Opinion, re PCT Application No. PCT/US2010/024378, mailing date Oct. 13, 2010.

PCT, International Search Report and Written Opinion, re PCT Application No. PCT/US2010/043760, mailing date Mar. 3, 2011.

PCT, The International Search Report and Written Opinion of the International Searching Authority, mailed Sep. 9, 2009, for case PCT/US2009/032028.

Progue, Brian W. et al., "Analysis of acetic acid-induced whitening of high-grade squamous intraepitheliallesions," Journal of Biomedical Optics; Oct. 2001; 6(4):397-403.

Raij, A.B., et al., Comparing Interpersonal Interactions with a Virtual Human to Those with a Real Human; IEEE Transactions on Visualization and Computer Graphics 13(3), 443-457 (2007).

Raz et al, Real-Time Magnetic Resonance Imaging-Guided Focal Laser Therapy in Patients with Low-Risk Prostate Cancer, European Urology 58, pp. 173-177. Mar. 12, 2010.

Robinett et al., "A Computational Model for the Stereoscopic Optics of a Head-Mounted Display," SPIE vol. 1457, Stereoscopic Displays and Applications II, pp. 140-160 (1991).

Rolland et al., Towards Quantifying Depth and Size Perception in Virtual Environments, Presence: Teleoperators and Virtual Environments, Winter 1995, vol. 4, Issue 1, pp. 1-21 and 24-49.

Rosenthal, Michael et al., "Augmented Reality Guidance for Needle Biopsies: An Initial Randomized, Controlled Trial in Phantoms," Proceedings of Medical Image Analysis, Sep. 2002, vol. 6(3), pp. 313-320, available from www.cs.unc.edu/~fuchs/publications/AugRealGuida_NeedleBiop02.pdf, printed Sep. 20, 2007, 8 pages.

Rosenthal, Michael et al., "Augmented Reality Guidance for Needle Biopsies: A Randomized, Controlled Trial in Phantoms," Proceedings of MICCAI 2001, eds. W. Niessen and M. Viergever, Lecture Notes in Computer Science, 2001, vol. 2208, pp. 240-248, available from www.cs.unc.edu/~us/AugmentedRealityAssistance.pdf, printed Sep. 20, 2007, 9 pages.

Screenshots from video produced by the University of North Carolina, produced circa 1992, Screenshots from video produced by the University of North Carolina, produced circa 1992.

Splechtna, Fuhrmann A. et al., Comprehensive calibration and registration procedures for augmented reality; Proc. Eurographics Workshop on Virtual Environments 2001,219-228 (2001).

(56) References Cited

OTHER PUBLICATIONS

State et al., "Case Study: Observing a Volume Rendered Fetus within a Pregnant Patient," Proceedings of IEEE Visualization 1994, pp. 364-368, available from www.cs.unc.edu/~fuchs/publications/cs-ObservVolRendFetus94.pdf, printed Sep. 20, 2007, 5 pages.

State et al., "Interactive Volume Visualization on a Heterogenous Message-Passing Multicomputer," Proceedings of 1995 Symposium on Interactive 3D Graphics, 1995, pp. 69-74, 208, available from www.cs.unc.edu/~andrei/pubs/1995_I3D_vol2_Mac.pdf, printed Sep. 20, 2007.

State et al., "Simulation-Based Design and Rapid Prototyping of a Parallax-Free, Orthoscopic Video See-Through Head-Mounted Display," Proceedings of International Symposium on Mixed and Augmented Reality (ISMAR) 2005, available from www.cs.unc.edu/~andrei/pubs/2005_ISMAR_VSTHMD_design.pdf, printed Sep. 20, 2007, 4 pages.

State et al., "Stereo Imagery from the UNC Augmented Reality System for Breast Biopsy Guidance" Proc. Medicine Meets Virtual Reality (MMVR) 2003 (Newport Beach, CA, Jan. 22-25, 2003).

State et al., "Superior Augmented Reality Registration by Integrating Landmark Tracking and Magnetic Tracking," ACM SIGGRAPH Computer Graphics, Proceedings of SIGGRAPH 1996, pp. 429-438, available from www.cs.princeton.edu/courses/archive/fall01/cs597d/papers/state96.pdf, printed Sep. 20, 2007, 10 pages.

State et al., "Technologies for Augmented Reality Systems: Realizing Ultrasound-Guided Needle Biopsies," Computer Graphics, Proceedings of SIGGRAPH 1996, pp. 429-438, available from www.cs.princeton.edu/courses/archive/fall01/cs597d/papers/state96.pdf, printed Sep. 20, 2007.

State, Andrei "Exact Eye Contact with Virtual Humans." Proc. IEEE International Workshop on Human Computer Interaction 2007 (Rio de Janeiro, Brazil, Oct. 20, 2007), pp. 138-145.

Takagi et al., "Development of a Stereo Video See-through HMD for AR Systems," IEEE, pp. 68-77 (2000).

Ultraguide 1000 System, Ultraguide, www.ultraguideinc.com, 1998.

Van Staveren et al., "Light Scattering in Intralipid—10% in the wavelength range of 400-1100 nm," Applied Optics; Nov. 1991; 30(31):4507-4514.

Viola et al., "Alignment by Maximization of Mutual Information," International Journal of Computer Vision, vol. 24, No. 2, pp. 1-29 (1997).

Viola, Paul A., Alignment by Maximization of Mutual Information, Ph.D. Dissertation, MIT-Artificial Intelligence Laboratory Technical Report No. 1548 (Jun. 1995).

Ware et al., "Dynamic Adjustment of Stereo Display Parameters," IEEE Transactions on Systems, Many and Cybernetics, 28(1):1-19 (1998).

Watson et al., "Using Texture Maps to Correct for Optical Distortion in Head-Mounted Displays," Proceedings of the Virtual Reality Annual Symposium '95, IEEE, pp. 1-7 (1995).

Welch, Hybrid Self-Tracker: An Inertial/Optical Hybrid Three-Dimensional Tracking System, University of North Carolina Chapel Hill Department of Computer Science, TR 95-048 (1995).

Yinghui et al., Real-Time Deformation Using Modal Analysis on Graphics Hardware, Graphite 2006, Kuala Lumpur, Malaysia, Nov. 29-Dec. 2, 2006.

Zitnick et al., "Multi-Base Stereo Using Surface Extraction," Visual Interface Inc., (Nov. 24, 1996).

U.S. Appl. No. 11/828,826, filed Jul. 26, 2007, Keller et al.

Azuma et al., "Improving Static and Dynamic Registration in an Optical See-Through HMO," Proceedings of SIGGRAPH '94, Computer Graphics, Annual Conference Series, 1994, 197-204 (1994).

Badler et al., "Simulating Humans: Computer Graphics, Animation, and Control," Oxford University Press (1993).

Fuchs, et al.: "Optimizing a Head-Tracked Stereo Display System to Guide Hepatic Tumor Ablation," Departments of Computer Sciences and Radiology, and School of Medicine, University of North Carolina at Chapel Hill; InnerOptic Technology, Inc. 2008.

Fuhrmann et al. "Comprehensive calibration and registration procedures for augmented reality," Proc. Eurographics Workshop on Virtual Environments 2001, 219-228 (2001).

http://www.planar.com/products/flatpanel_monitors/stereoscopic/ (Printed Dec. 29, 2011).

Keller et al., "What is it in Head Mounted Displays (MDs) that really make them all so terrible?," pp. 1-8 (1998).

Lee, et al., "Modeling Real Objects Using Video See-Through Augmented Reality," Proceedings of the Second International Symposium on Mixed Reality, ISMR 2001, pp. 19-26 (Mar. 14-15, 2001).

State et al., "Superior Augmented Reality Registration by Integrating Landmark Tracking and Magnetic Tracking," ACM SIGGRAPHG Computer Graphics, Proceedings of SIGGRAPH 1996, pp. 1-8 (Aug. 1996).

State, et al.: Contextually Enhanced 3D Visualization for Multi-Born Tumor Ablation Guidance, Departments of Computer Science and Radiology, and School of Medicine, University of North Carolina at Chapel Hill; InnerOptic Technology, Inc. 2008, Chapel Hill, NC, pp. 70-77.

Symons et al., "What are You Looking at? Acuit for Triadic Eye Gaze," J. Gen. Psychology 131(4), pp. 451-469 (2004).

Takacs et al., "The Virtual Human Interface: A Photorealistic Digital Human," IEEE Computer Graphics and Applications 23(5), pp. 38-45 (2003).

Takayama et al., "Virtual Human with Regard to Physical Contact and Eye Contact," Entertaining Computing 2005, LNCS, vol. 3711, pp. 268-278 (2005).

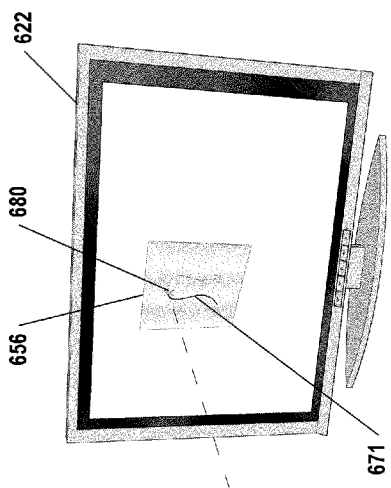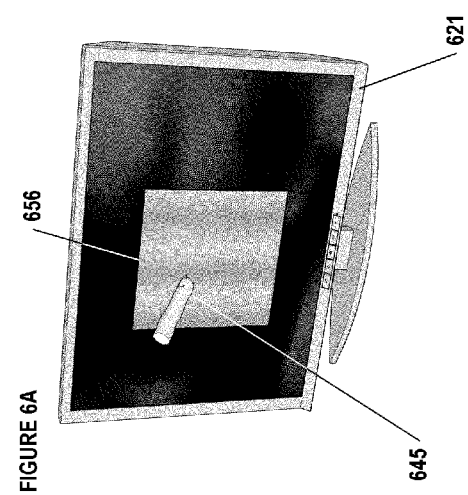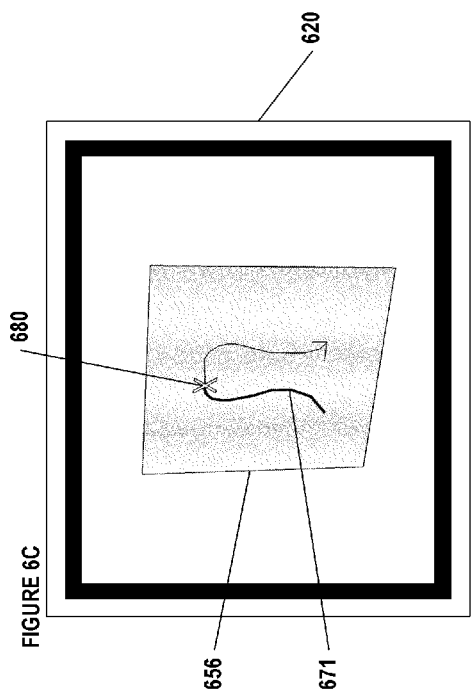

IMAGE ANNOTATION IN IMAGE-GUIDED MEDICAL PROCEDURES

CROSS-REFERENCE TO RELATED APPLICATIONS

This application is a continuation of U.S. application Ser. No. 13/014,596, which claims benefit to U.S. Provisional Patent Application No. 61/322,991 filed Apr. 12, 2010, and U.S. Provisional Patent Application No. 61/387,132, filed Sep. 28, 2010. Each of the provisional applications, 61/322,991 and 61/387,132 is incorporated by reference herein in its entirety for all purposes.

FIELD

The embodiments herein disclosed relate to computer-assisted medical procedures and more specifically to image annotation in image-guided medical procedures.

BACKGROUND

The past few decades have seen incredible developments of technology and systems for computer-assisted, image-based, and image-guided surgery and other medical procedures. These advances in image-guided surgery are tied in part to technical and scientific improvements in imaging and three-dimensional (3D) computer graphics. For example, some of the early work of in this field in the late 1980's provided new 3D graphics rendering techniques, medical image shape detection, and head-mounted displays. These are some of the building blocks of later image-guided surgery systems developed in the mid-1990's and thereafter. Image-guided surgery makes use of imaging to aid a surgeon in performing more effective and more accurate surgeries.

Current image-guided surgery systems, however, do not provide adequate mechanisms to annotate images. The process of annotation is difficult and extremely time-consuming. Further, it would be difficult, disruptive, and time consuming for a surgeon or other operator to annotate an image during a medical procedure.

One or more of these problems and others are addressed by the systems, methods, devices, computer-readable media, techniques, and embodiments described herein. That is, some of the embodiments described herein may address one or more issues, while other embodiments may address different issues.

SUMMARY

Presented herein are methods, systems, devices, and computer-readable media for image annotation in image-guided medical procedures. In some embodiments, pose information is determined for visualizable medical data and changing pose information is determined for a medical device over time. An annotation in 3D space may be generated based on the pose information over time for the medical device and the pose information for the visualizable medical data; and image guidance information may be generated based at least in part on the annotation in 3D space. A graphical rendering of the image guidance information may be displayed on one or more displays.

In some embodiments, a system may determine device type information for a first medical device; real-time emplacement information for the first medical device; and real-time emplacement information for a second medical device. The system may also determine the real-time relative emplacements of the first and second medical devices with the computer system and real-time prediction information for the first medical device. The image guidance system may then generate image guidance information based on the real-time relative emplacements of the first and second medical devices, the real-time prediction information for the first medical device, and data related to the second medical device. A graphical rendering of the image guidance information may be displayed on one or more displays. It is possible that determining changing pose information for the medical device over time include determining the changing pose information for the medical device over time relative to a 2D screen displaying the visualizable medical data; and/or generating the annotation in 3D space based on the pose information over time for the medical device and the pose information for the visualizable medical data may include determining the annotation in 3D space based at least in part on the 2D pose information.

Numerous other embodiments are described throughout herein. Although various embodiments are described herein, it is to be understood that not necessarily all objects, advantages, features or concepts need to be achieved in accordance with any particular embodiment. Thus, for example, those skilled in the art will recognize that the invention may be embodied or carried out in a manner that achieves or optimizes one advantage or group of advantages as taught or suggested herein without necessarily achieving other objects or advantages as may be taught or suggested herein.

All of these embodiments are intended to be within the scope of the invention herein disclosed. These and other embodiments will become readily apparent to those skilled in the art from the following detailed description having reference to the attached figures, the invention not being limited to any particular disclosed embodiment(s).

BRIEF DESCRIPTION OF THE DRAWINGS

FIGS. 6A-6C illustrate three additional example interfaces for image annotation in image-guided medical procedures.

DETAILED DESCRIPTION

Overview

Figure 2A:
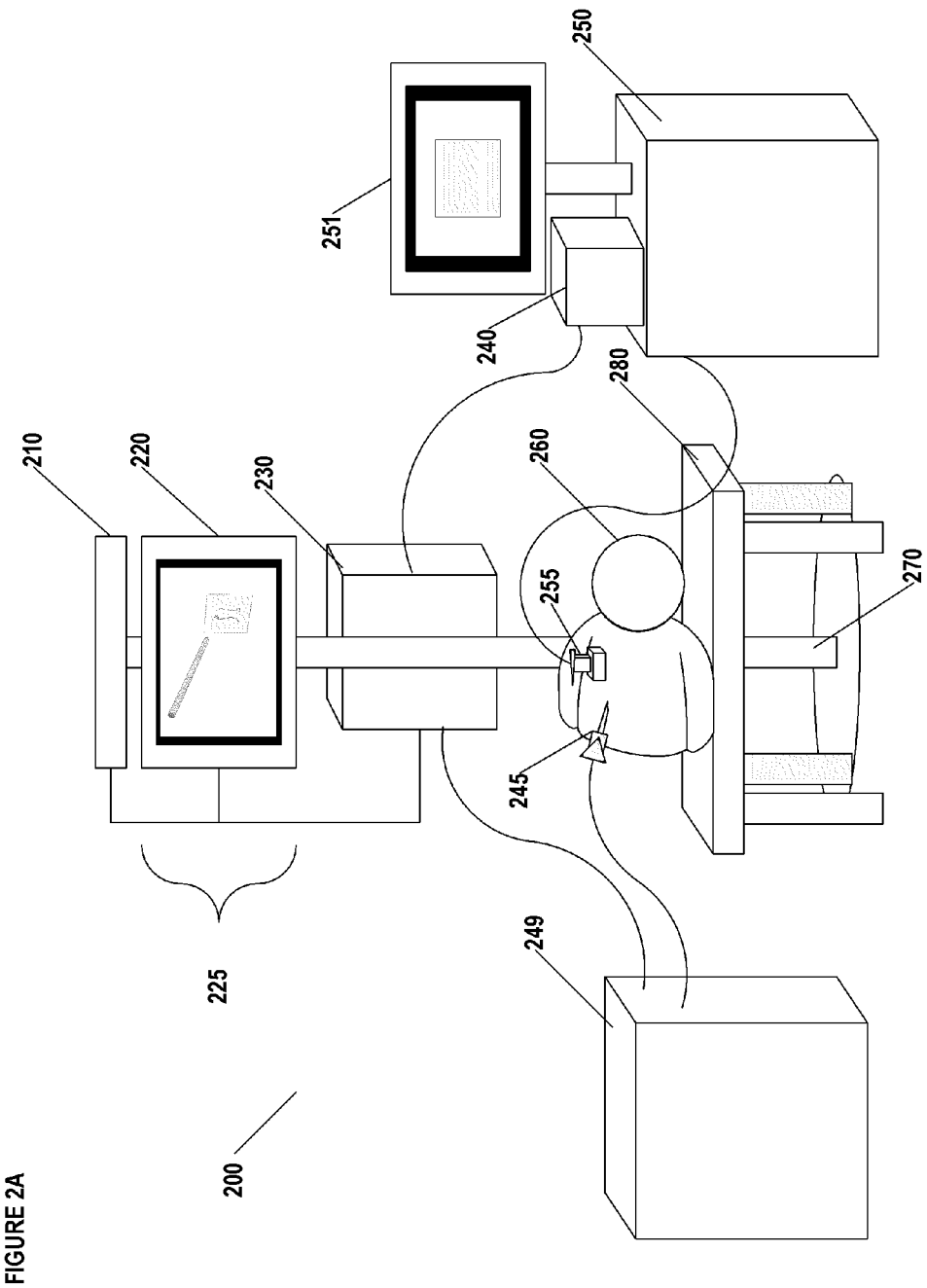
FIGS. 2A and 2B illustrate example systems for image annotation in image-guided medical procedures.
Figure 2B:
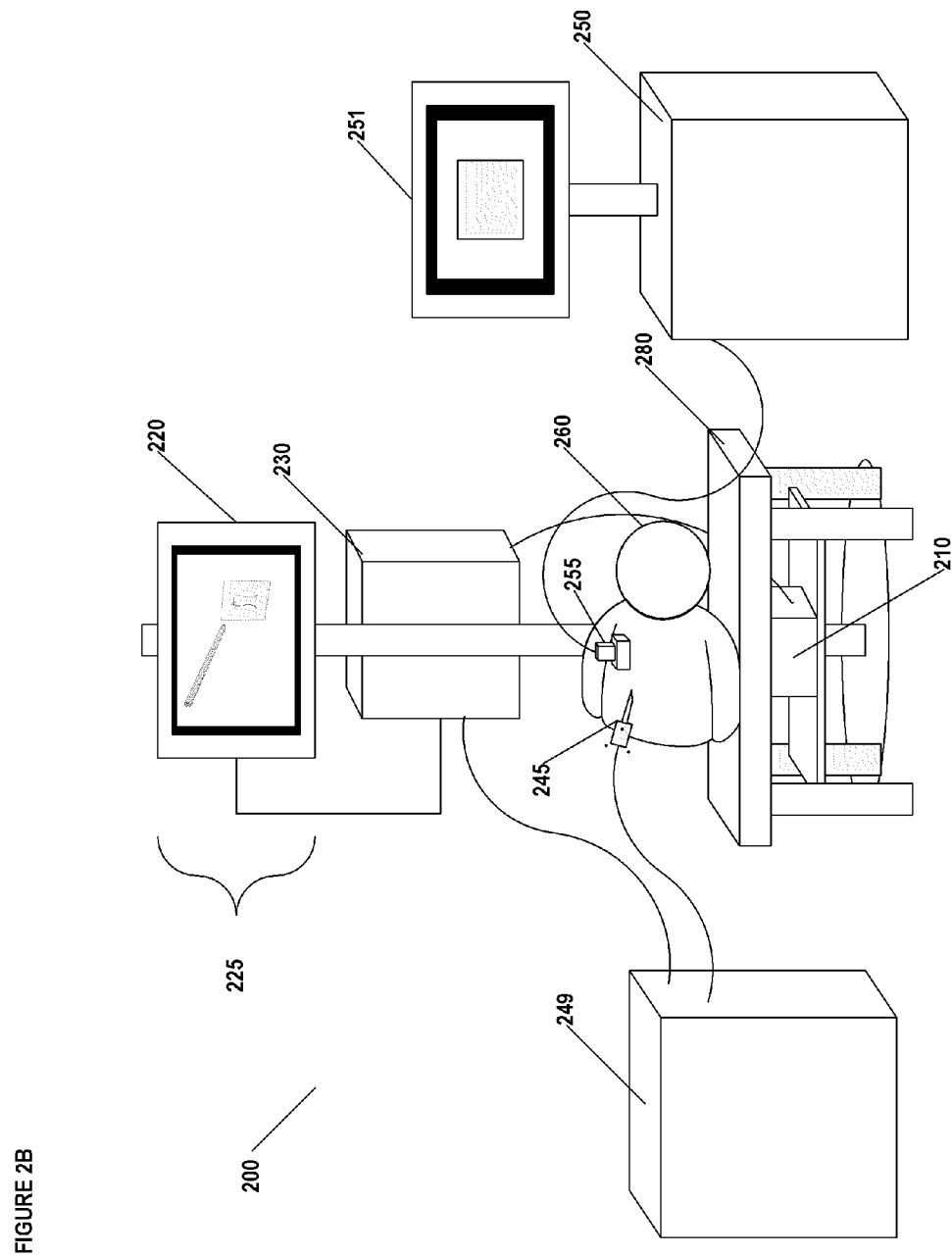

In some embodiments herein, an operator, surgeon or other medical practitioner may annotate images during an image-guided medical procedure. In some embodiments, the operator may use medical devices that are typically present during the medical procedure to annotation the medical images. As depicted in FIGS. 2A and 2B, and as described more below, an operator, such as a surgeon or other medical practitioner, may use a first medical device 245 (e.g., an ablation needle) and a second medical device 255 (e.g., an ultrasound transducer) during a medical procedure and one or both of these medical devices 245 and 255 may be used for image annotation.

Figure 1A:
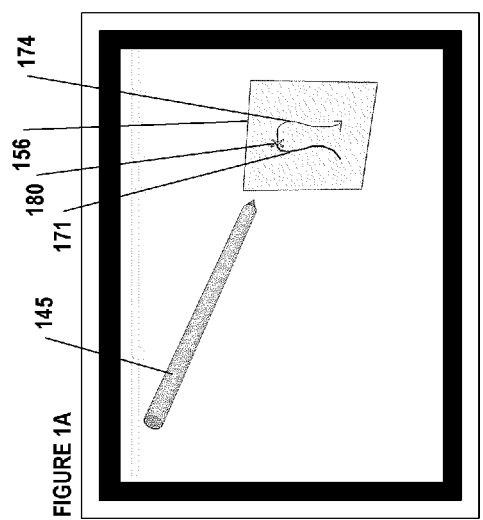
FIGS. 1A-1D illustrate four example interfaces for image annotation in image-guided medical procedures.
Figure 1B:
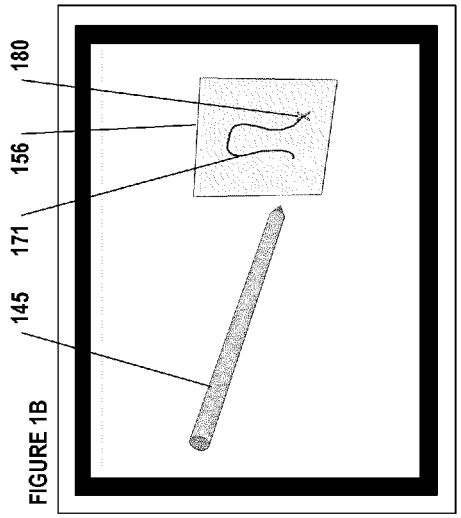

FIGS. 1A-1D illustrate examples of image annotation in image-guided medical procedures. FIGS. 1A-1D show a representation on a computer screen 120 of an annotation being made with a medical device (represented on the display 120 as medical device 145). The medical device may be used to annotate an image 156. FIG. 1A illustrates the manipulation of a needle 145 pointing at an image 156 (e.g., an ultrasound image 156). The operator can make an annotation by moving the needle 145 through space in order to draw curve 171 on image 156. Arrow 174 may indicate the direction that the operator plans to or will draw in the future. In some embodiments, arrow 174 is not displayed. Indicator 180 may represent the place on image 156 currently pointed to by needle 145. Indicator 180 may be any appropriate indicator such as an "X," an arrow, a differently-colored area, etc. In FIG. 1B the operator has further moved needle 145 in order to complete the annotation 171 on image 156. As is depicted in FIG. 1B, the indicator 180 of the intersection between the axis of the needle 145 and the image 156 has now reached the lower-right quadrant of the image 156.

The image 156 may be associated with a medical device, such as an ultrasound transducer (not pictured in FIGS. 1A-1D). The image 156 may be an ultrasound image 156, or the image 156 may be a slice or image from other 3D visualizable medical data such as is described in Image Management in Image-Guided Medical Procedures, to Sharif Razzaque et al., filed concurrently herewith, which is incorporated by reference for all purposes.

Figure 1C:
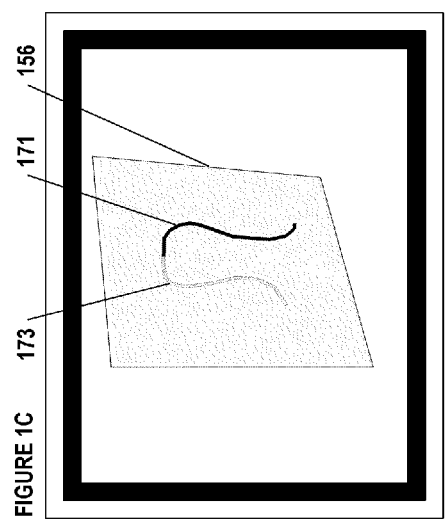

The annotation 171, although it has been drawn on an image 156, may actually be located in 3D space—defined by the placement of the image 156 and the annotation 171. FIG. 1C depicts image 156, associated with the ultrasound transducer turned or rotated about its vertical axis (axis not depicted in FIG. 1C). Therefore, part of the annotation 171 is depicted in front of the image 156, and part of the annotation 173 is behind the image 156, thus illustrating the existence in 3D space of the annotation 171/173. The location and display of annotations in 3D space will allow an operator to make an annotation for a feature (e.g., a tumor, cyst, or vein), and allow her to locate that feature again later.

Figure 1D:
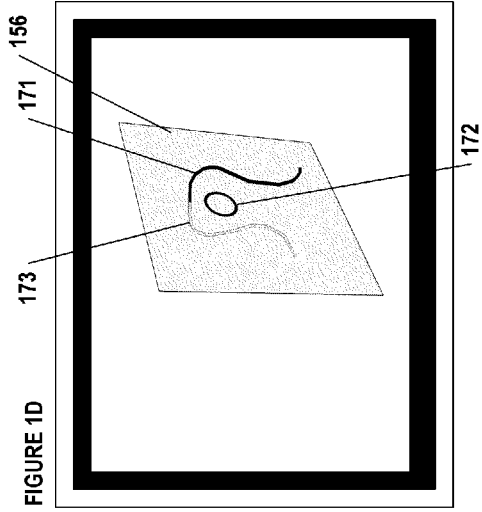

FIG. 1D illustrates that an operator may make a second annotation 172 on the image 156. Part of the first annotation 171 is in front of the image 156 and part 173 is behind. By manipulating the pose of the image 156 (by manipulating the ultrasound transducer), the operator can choose new locations within 3D space for annotations. As noted above, the annotations may be for a blood vessel, tumor, or any other object or location of interest for the operator. There need not even be a particular object in the medical image that the operator is annotating. The operator may, for example, sign her name or write a note. For example, an operator may circle or make marks near multiple tumors, trace a line such as annotation 171 along a vein or artery, etc. In some embodiments, if the operator moves image 156 during annotation, the operator may make non-planar annotation (see, e.g., FIGS. 4 and 5). As such, the operator may be able to make a sphere or other non-planar annotation in order to annotate the volumetric aspects of a feature of interest. For example, the operator may draw the outline of a sphere around a tumor or cyst.

Using embodiments described herein, a radiologist or other practitioner is not limited to marking tumors or other anatomical references on individual slices of CT scans. Instead, the radiologist may move in an intuitive manner through the CT scan. Further, various embodiments may decrease the time it takes to annotate an image, and/or to display those annotations, during a medical procedure, thereby reducing cost.

By allowing multiple annotations and by enabling the operator to place annotations in 3D space, various embodiments herein allow the operator to mark multiple objects of interest and view the location of those marks of interest at a later time. The annotations may be displayed using any display technique, such as those described in Image Management in Image-Guided Medical Procedures, to Sharif Razzaque et al., filed concurrently herewith and incorporated by reference above for all purposes.

Images may be annotated using embodiments herein during all a portion of a medical procedure. In one embodiment, the image annotation will only occur during an image annotation "session" (e.g. a period of time during which image annotation is performed, and before and after which, image annotation is not performed). An image annotation "session" may be initiated and/or terminated by the operator performing a key stroke, issuing a command (such as a verbal command), performing a gesture with a medical device or hand, pressing a button on the medical device, pressing a foot pedal, pressing a button on the medical device (e.g., a button on a Wacom pen), etc.

As used herein, the term "medical device" is a broad term that encompasses but is not limited to a device, item, or part used in the medical procedure. For example, a medical device could include an ablation needle, an ultrasound transducer, a cauterizer, a scalpel, a glove covering an operator's hand, the operator's hand or finger, etc. The medical device used for pose information could even be the operator's head, eyes, or gaze direction. Pose information for the medical device may be obtained using any system, device, method, or technique, such as those disclosed herein.

Example Systems

FIG. 2A illustrates a first exemplary system for image management in image guided surgery. FIG. 2B illustrates a second exemplary system for image management in image guided surgery. In many respects, the embodiments illustrated by FIGS. 2A and 2B are similar and use similar numbering. Where the two are different, those differences are noted. The differences between the two figures may include that, in FIG. 2A, two position sensing units 210 and 240 are shown, whereas in FIG. 2B, only a single position sensing unit 210 is shown.

In one embodiment, position sensing units 210 and 240 may be tracking systems 210 and 240 and may track surgical instruments 245 and 255 and provide data to the image guidance unit 230. The image guidance unit 230 may process or combine the data and show image guidance data on display 220. This image guidance data may be used by a physician to guide a procedure and improve care. There are numerous other possible embodiments of system 200. For example, many of the depicted modules may be joined together to form a single module and may even be implemented in a single computer or machine. Further, position sensing units 210 and 240 may be combined and track all relevant surgical instruments 245 and 255, as discussed in more detail below and exemplified in FIG. 2B. Additional imaging units 250 may be included and combined imaging data from the multiple imaging units 250 may be processed by image guidance unit 230 and shown on display unit 220. Additionally, two or more surgical systems 249 may also be included.

Information about and from multiple surgical systems 249 and/or attached surgical instruments 245 may be processed by image guidance unit 230 and shown on display 220. These and other possible embodiments are discussed in more detail below. Imaging unit 250 may be coupled to image guidance unit 230. In one embodiment, imaging unit 250 may be coupled to a second display unit 251. The second display unit 251 may display imaging data from imaging unit 250. The imaging data displayed on display unit 220 and displayed on second display unit 251 may be, but are not necessarily, the same. In an embodiment, the imaging unit 250 is an ultrasound machine 250, the movable imaging device 255 is an ultrasound transducer 255 or ultrasound 255, and the second display unit 251 is a display associated with the ultrasound machine 250 that displays the ultrasound images from the ultrasound machine 250. In one embodiment, a movable imaging unit 255 may not be connected directly to an imaging unit 250, but may instead be connected to image guidance unit 230. The movable imaging unit 255 may be useful for allowing a user to indicate what portions of a first set of imaging data should be displayed. For example, the movable imaging unit 255 may be an ultrasound transducer 255 or a tracked operative needle or other device 255, for example, and may be used by a user to indicate what portions of imaging data, such as a pre-operative CT scan, to show on a display unit 220 as image 225. Further, in some embodiments, there could be a third set of pre-operative imaging data that could be displayed with the first set of imaging data.

In some embodiments, system 200 comprises a first position sensing unit 210, a display unit 220, and second position sensing unit 240 (if it is included) all coupled to image guidance unit 230. In one embodiment, first position sensing unit 210, display unit 220, and image guidance unit 230 are all physically connected to stand 270. Image guidance unit 230 may be used to produce images 225 that are displayed on display unit 220. The images 225 produced on display unit 220 by the image guidance unit 230 may be determined based on ultrasound or other visual images from first surgical instrument 245 and second surgical instrument 255. For example, if first surgical instrument 245 is an ablation needle 245 and second surgical instrument 255 is an ultrasound probe 255, then images 225 produced on display 220 may include the video or images from the ultrasound probe 255 combined with graphics, such as projected needle drive or projected ablation volume, determined based on the pose of ablation needle 245. If first surgical instrument 245 is an ultrasound probe 245 and second surgical instrument 255 is a laparoscopic camera 255, then images 225 produced on display 220 may include the video from the laparoscopic camera 255 combined with ultrasound data superimposed on the laparoscopic image. More surgical instrument may be added to the system. For example, the system may include an ultrasound probe, ablation needle, laparoscopic camera, cauterizer, scalpel and/or any other surgical instrument or medical device. The system may also process and/or display previously collected data, such as preoperative CT scans, X-Rays, MRIs, laser scanned 3D surfaces etc.

The term "pose" as used herein is a broad term encompassing its plain and ordinary meaning and may refer to, without limitation, emplacement, position, orientation, the combination of position and orientation, or any other appropriate location information. In some embodiments, the imaging data obtained from one or both of surgical instruments 245 and 255 may include other modalities such as a CT scan, MRI, open-magnet MRI, optical coherence tomography, positron emission tomography ("PET") scans, fluoroscopy, ultrasound, or other preoperative, or intraoperative 2D or 3D anatomical imaging data. In some embodiments, surgical instruments 245 and 255 may also be scalpels, implantable hardware, or any other device used in surgery. Any appropriate surgical system 249 or imaging unit 250 may be coupled to the corresponding medical instruments 245 and 255.

As noted above, images 225 produced may also be generated based on live, intraoperative, or real-time data obtained using second surgical instrument 255, which is coupled to second imaging unit 250. The term "real-time" as used herein is a broad term and has its ordinary and customary meaning, including without limitation instantaneously or nearly instantaneously. The use of the term realtime may also mean that actions are performed or data is obtained with the intention to be used immediately, upon the next cycle of a system or control loop, or any other appropriate meaning Additionally, as used herein, real-time data may be data that is obtained at a frequency that would allow a surgeon to meaningfully interact with the data during surgery. For example, in some embodiments, real-time data may be a medical image of a patient that is updated one time per second or multiple times per second.

Second surgical instrument 255 may be coupled to second position sensing unit 240. Second position sensing unit 240 may be part of imaging unit 250 or it may be separate. Second position sensing unit 240 may be used to determine the pose of second surgical instrument 255. In some embodiments, first and/or second position sensing units 210 and/or 240 may be magnetic trackers and magnetic may be coils coupled to surgical instruments 245 and/or 255. In some embodiments, first and/or second position sensing units 210 and/or 240 may be optical trackers and visually-detectable fiducials may be coupled to surgical instruments 245 and/or 255.

Images 225 may be produced based on intraoperative or real-time data obtained using first surgical instrument 245, which is coupled to first surgical system 249. In FIGS. 2A and 2B, first surgical system 249 is shown as coupled to image guidance unit 230. The coupling between the first surgical system 249 and image guidance unit 230 may not be present in all embodiments. In some embodiments, the coupling between first surgical system 249 and image guidance unit 230 may be included where information about first surgical instrument 245 available to first surgical system 249 is useful for the processing performed by image guidance unit 230. For example, in some embodiments, first surgical instrument 245 is an ablation needle 245 and first surgical system 249 is an ablation system 249. In some embodiments, it may be useful to send a signal about the relative strength of planned ablation from ablation system 249 to image guidance unit 230 in order that image guidance unit 230 can show a predicted ablation volume. In other embodiments, first surgical system 249 may not be coupled to image guidance unit 230. Example embodiments including images and graphics that may be displayed are included below.

In an embodiment, first position sensing unit 210 tracks the pose of first surgical device 245. First position sensing unit 210 may be an optical tracker 210 and first surgical device 245 may have optical fiducials attached thereto. The pose of optical fiducials may be detected by first position sensing unit 210, and, therefrom, the pose of first surgical device 245 may be determined.

In various embodiments, as depicted in FIG. 2B, a single position sensing unit 210 may track both first medical device 245 and second medical device 255. In FIG. 2B, in some embodiments, position sensing unit 210 is a magnetic tracker and is mounted below a surgical table 280. Such an arrangement may be useful when the tracking volume of the position sensing unit 210 is dependent on the location of the position sensing unit, as with many magnetic trackers. Magnetic tracking coils may be mounted in or on the medical devices 245 and 255.

In some embodiments, either or both of the first position sensing unit 210 and the second position sensing unit 240 may be an Ascension Flock of Birds, Nest of Birds, driveBAY, medSAFE, trakSTAR, miniBIRD, MotionSTAR, pciBIRD, or Calypso 4D Localization System and tracking units attached to the first and/or second surgical or medical devices 245 and 255 may be magnetic tracking coils. The term "tracking unit," as used herein, is a broad term encompassing its plain and ordinary meaning and includes without limitation all types of magnetic coils or other magnetic field sensing devices for use with magnetic trackers, fiducials or other optically detectable markers for use with optical trackers, such as those discussed above and below. Tracking units could also include optical position sensing devices such as the HiBall tracking system and the first and second position sensing units 210 and 240 may be part of a HiBall tracking systems. Tracking units may also include a GPS device or signal emitting device that would allow for tracking of the position and, optionally, orientation of the tracking unit. In some embodiments, a signal emitting device might include a radio-frequency identifier (RFID). In such embodiments, the first and/or second position sensing unit 210 and 240 may take in the GPS coordinates of the tracking units or may, for example, triangulate the radio frequency signal being emitted by the RFID associated with tracking units. The tracking systems may also include one or more 3D mice.

In some embodiments, either or both of the first position sensing unit 210 and the second position sensing unit 240 may be an Aurora® Electromagnetic Measurement System using sensor coils for tracking units attached to the first and/or second surgical devices 245 and 255. In some embodiments, either or both of the first position sensing unit 210 and the second position sensing unit 240 may also be an optical 3D tracking system using fiducials. Such optical 3D tracking systems may include the NDI Polaris Spectra, Vicra, Certus, PhaseSpace IMPULSE, Vicon MX, InterSense IS-900, NaturalPoint OptiTrack, Polhemus FastTrak, IsoTrak, or Claron MicronTracker2. In some embodiments, either or both of position sensing units 210 and 240 may each be an inertial 3D tracking system comprising a compass, accelerometer, tilt sensor and/or gyro, such as the InterSense InertiaCube or the Wii controller. In some embodiments, either or both of position sensing units 210 and 240 may be attached to or affixed on the corresponding surgical device 245 and 255. In some embodiments, the position sensing units, 210 and 240, may include sensing devices such as the HiBall tracking system, a GPS device, or signal emitting device that would allow for tracking of the position and, optionally, orientation of the tracking unit. In some embodiments, a position sensing unit 210 or 240 may be affixed to either or both of the surgical devices 245 and 255. The surgical devices 245 or 255 may be tracked by the position sensing units 210 or 240. A world reference, such as the display 220 may also be tracked by the position sensing unit 210 or 240 in order to determine the poses of the surgical devices 245 and 255 with respect to the world. Devices 245 and 255 may also include or have coupled thereto one or more accelerometers, which may be used to estimate movement, position, and location of the devices.

In an embodiment, the display unit 220 displays 3D images to a user, such as a physician. Stereoscopic 3D displays separate the imagery shown to each of the user's eyes. This can be accomplished by a stereoscopic display, a lenticular auto-stereoscopic display, or any other appropriate type of display. The display 220 may be an alternating row or alternating column display. Example alternating row displays include the Miracube G240S, as well as Zalman Trimon Monitors. Alternating column displays include devices manufactured by Sharp, as well as many "auto-stereoscopic" displays (e.g., Philips). Display 220 may also be a cathode ray tube. Cathode Ray Tube (CRT) based devices, may use temporal sequencing, showing imagery for the left and right eye in temporal sequential alternation; this method may also be used by newer, projection-based devices, as well as by 120-Hz-switchable liquid crystal display (LCD) devices.

In one embodiment, a user may wear a head mounted display in order to receive 3D images from the image guidance unit 230. In such embodiments, a separate display, such as the pictured display unit 220, may be omitted. The 3D graphics may be produced using underlying data models, stored in the image guidance unit 230 and projected onto one or more 2D planes in order to create left and right eye images for a head mount, lenticular, or other 3D display. The underlying 3D model may be updated based on the relative poses of the various devices 245 and 255, as determined by the position sensing unit(s), and/or based on new data associated with the devices 245 and 255. For example, if the second device is an ultrasound probe 255, then the underlying data model may be updated to reflect the most recent ultrasound image. If the first device 245 is an ablation needle, then the underlying model may be updated to reflect any changes related to the needle, such as power or duration information. Any appropriate 3D graphics processing may be used for rendering including processing based on OpenGL, Direct3D, Java 3D, etc. Whole, partial, or modified 3D graphics packages may also be used, such packages including 3DS Max, SolidWorks, Maya, Form Z, Cybermotion 3D, VTK, Slicer, or any others. In some embodiments, various parts of the needed rendering may occur on traditional or specialized graphics hardware. The rendering may also occur on the general CPU, on programmable hardware, on a separate processor, be distributed over multiple processors, over multiple dedicated graphics cards, or using any other appropriate combination of hardware or technique.

Regardless of the rendering implementation, in various embodiments, the volume can be displayed from several different perspectives:

From that of the physician, using a position sensor on the ultrasound transducer and optionally on the physician as well;
From that of the camera, x-ray radiation emitter, or imager;
From that of the ultrasound transducer;
From that of the needle or ablation device.

One or more modules, units, devices, or elements of various embodiments may be packaged and/or distributed as part of a kit. For example, in one embodiment, an ablation needle, tracking elements, 3D viewing glasses, and/or a portion of an ultrasound wand may form a kit. Other embodiments may have different elements or combinations of elements grouped and/or packaged together. Kits may be sold or distributed separately from or with the other portions of the system.

There are numerous other examples of image guidance systems which may use, incorporate, support, or provide for the techniques, methods, processes, and systems described herein, such as the 3D computer-graphics-based assigned to InnerOptic Technologies, Inc. that provides for displaying guidance data from multiple sources, U.S. application Ser. No. 11/833,134, filed Aug. 2, 2007, the contents of which are incorporated by reference herein in their entirety for all purposes. The image guidance may also be performed at least in part using the techniques described in U.S. patent application Ser. No. 11/828,826, filed Jul. 26, 2007, U.S. Pat. No. 7,728,868, U.S. patent application Ser. No. 12/299,899, U.S. patent application Ser. No. 12/483,099, U.S. patent application Ser.

No. 12/893,123, U.S. patent application Ser. No. 12/842,261, and/or U.S. patent application Ser. No. 12/703,118, each of which is incorporated by reference herein in its entirety for all purposes.

Depicting Combinations of Graphics

Figure 8:
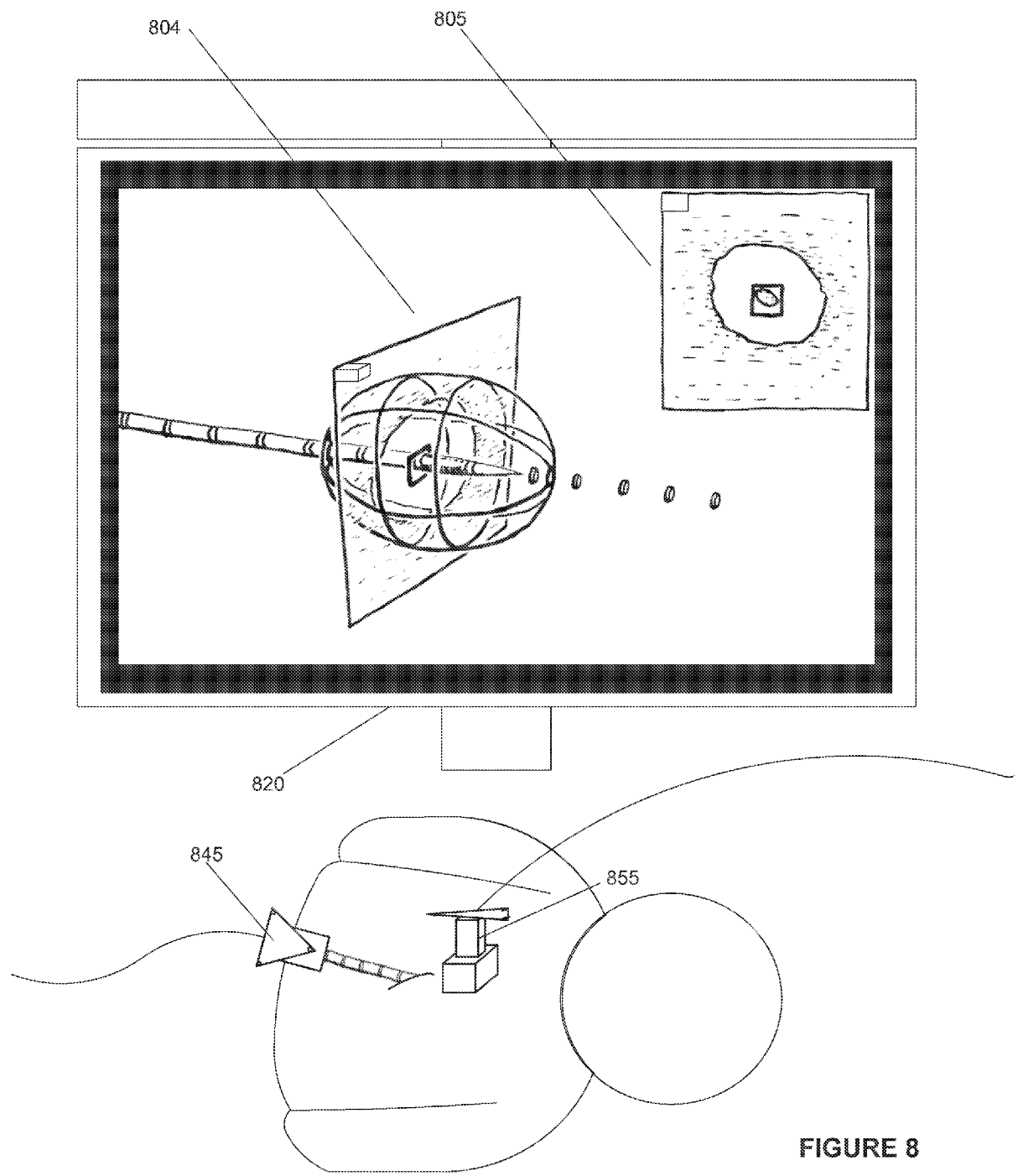
FIG. 8 illustrates an example of displaying image guidance data.

As discussed herein, when there are multiple instruments or devices being used in a procedure, images, graphics, and data associated with the multiple instruments may be displayed to the physician. In some embodiments, as depicted in FIG. 8, when there are two devices 845 and 855 being used and tracked in a procedure, data, images, and graphics associated with those two images may be combinable and may be displayed on the same display. FIG. 8 depicts an ablation needle 845 and an ultrasound wand 855 being used during a procedure. Data associated with each of the devices 845 and 855 are displayed on the display 820.

The data from two or more devices may be combined and displayed based on their relative emplacements or poses. For example, an ultrasound image 804 may be displayed with respect to an ablation needle on a display 820 in a manner that estimates the relative emplacements or poses of an ultrasound wand 855 and ablation needle 845. This is depicted in FIG. 8. In FIG. 8, the graphics associated with the ablation needle 845, including the ablation volume and projected drive location are shown spatially located with the oriented planar ultrasound image on display 820. In this image 804, a tumor appears in the ultrasound image and the ablation needle is shown driven through the tumor. The ablation volume estimates where ablation would occur if it tissue were ablated at that time. The physician can see that the ablation volume appears to cover the tumor displayed in the ultrasound image.

Various embodiments include other combinations of graphics. For example, in some embodiments, data related to a single surgical instrument (such as an ablation needle, ultrasound wand, etc.) may be presented in more than one manner on a single display. Consider an embodiment in which device 845 is an ablation needle and device 855 is an ultrasound transducer. If a physician orients ultrasound transducer 855 such that it is perpendicular to the monitor, the 3D view of the ultrasound image would show only the edge and the ultrasound image would not be visible. In some embodiments, the image guidance system could track the physician's head using a position sensor, such as first and/or second position sensing units 210 and/or 240 of FIG. 2A or FIG. 2B. The physician then may be able to move her head to the side, so that she sees the ultrasound image from a different perspective.

In some embodiments, the image guidance system can constantly display an additional 2D view of the ultrasound image 805 (in screen space), simultaneous to the 3D depiction of the procedure, so that the ultrasound image is always visible, regardless of the orientation in which the physician holds the transducer. This is illustrated in FIG. 8. This display of the ultrasound data may be similar to what a physician is accustomed to seeing with traditional ultrasound displays. This may be useful to provide the physician with imaging to which she is accustomed and allows a physician to see the ultrasound data regardless of the then current orientation of the ultrasound wand with respect to the user.

In some embodiments, the 2D view 805 of an ultrasound image is depicted in the upper right corner of the monitor (though it can be placed in any corner). The guidance system can automatically (and continually) choose a corner in which to render the 2D view of the ultrasound image, based on the 3D position of the surgical instruments in the rendered scene. For example, in FIG. 8, ablation needle 845 may be held in the physician's left hand and the needle shaft is to the left of the 3D ultrasound image slice, so that the 2D ultrasound image 805 in the upper right corner of display 820 does not cover any of the 3D features of the needle (or vice-versa). If the needle were held in the physician's right hand, the virtual needle shaft would appear on the right side. To prevent the 2D ultrasound image in the corner of display 820 from covering the needle shaft, the system can automatically move it to a corner that would not otherwise be occupied by graphics or data.

In some embodiments, the system attempts to avoid having the 2D ultrasound image quickly moving among corners of the display in order to avoid overlapping with graphics and data in the display. For example, a function $f$ may be used to determine which corner is most suitable for the 2D ultrasound image to be drawn in. The inputs to $f$ may include the locations, in the screen coordinate system, of the displayed needle tip, the corners of the 3D ultrasound image, etc. In some embodiments, $f$'s output for any given point in time is independent $f$'s output in the previous frames, which may cause the ultrasound image to move among corners of the display rapidly. In some embodiments, the image guidance system will filter $f$'s output over time. For example, the output of a filter $g$, for any given frame, could be the corner which has been output by $f$ the most number of times over the last n frames, possibly weighting the most recent values for $f$ most heavily. The output of the filter $g$ may be used to determine in which corner of display 820 to display the 2D ultrasound image and the temporal filtering provided by $g$ may allow the 2D ultrasound image display to move more smoothly among the corners of the display 820.

In some embodiments, other appropriate virtual information can be overlaid on the 2D ultrasound image as well. Examples include: an indication of the distance between the needle's tip and the point in the plane of the ultrasound image that is closest to the needle tip; the cross section or outline of the ablation volume that intersects with the ultrasound slice; and/or the intersection point, box, outline, etc. between the needle's axis and the ultrasound image plane.

Methods for Image Annotation in Image-Guided Medical Procedures

Figure 3:
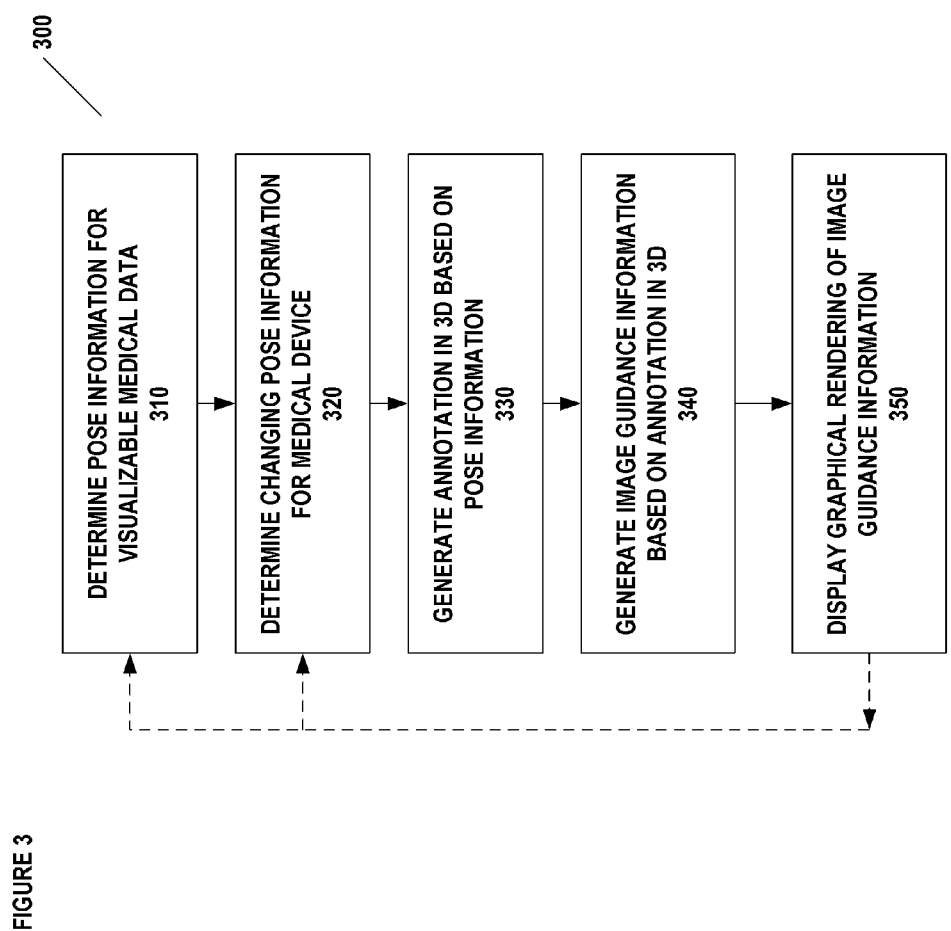
FIG. 3 is a flow diagram that illustrates an example method for image annotation in image-guided medical procedures.

FIG. 3 depicts a method 300 for image annotation in image-guided medical procedures. As just one example embodiment, pose information for an ultrasound transducer and its associated ultrasound image may be determined in block 310. In block 320, changing pose information for an ablation needle may be determined in block 320. The pose information may change as an operator moves the ablation needle and/or the ultrasound transducer. An annotation may be generated in block 330 based on, for example, the intersection of an axis of the ablation needle and the ultrasound image plane. Image guidance information may be generated in block 340 based on the annotation in 3D space (and include, e.g., the annotation, the ultrasound image, a depiction of the ablation needle, and/or other imaging or guidance information). In block 350, the image guidance information may be displayed.

In block 310, pose information for visualizable medical data is determined. "Visualizable medical data" is a broad term that encompasses its ordinary and customary meaning and includes, without limitation, any two-dimensional (2D) or 3D medical data that can be visualized. The visualizable medical data may also be volumetric and can include, without limitation, one or more of a CT scan, an MRI, other 3D preoperative imaging data, other volume data, segmented internal organs, segmented blood vessels, annotations, tumors, etc. The visualizable medical data may also include 2D medical data such as ultrasounds, X-rays, or segments or slices of 3D medical data.

In some embodiments, the visualizable medical data may be associated with a medical device, such as an ultrasound probe, etc., and the medical device may be tracked in the medical scene. In such embodiments, the pose information for the visualizable medical data may be determined in block 310 from the pose of the associated medical device (that is tracked in the medical scene). For example, if the visualizable medical data is associated with an ultrasound probe and the ultrasound probe is tracked, then the pose of the visualizable medical data can be determined from the pose of the ultrasound probe. This can be the case even if the visualizable medical data is not generated by the medical device. For example, if the medical device is an ultrasound transducer and the visualizable medical data is a slice or image from a CT scan that is being navigated using the ultrasound transducer (see, for example, Image Management in Image-Guided Medical Procedures, to Sharif Razzaque et al., filed concurrently herewith, which is incorporated by reference above for all purposes) then the pose for that slice or image from the CT scan can still be determined based on the pose of the medical device.

When navigating/visualizing CT or other volumetric data with a medical device such as an ultrasound transducer, pose information for the medical device may be updated over time. Pose information for the underlying volumetric visualizable medical data set may also be determined (e.g., relative to the medical scene). The pose information for the underlying volumetric visualizable medical data (e.g., a CT scan or other volumetric data) may be determined separately from the pose information of the medical device used to visualize the medical data. Further, in some embodiments, the pose information for the visualizable medical data may initially be determined in order to register or approximately register the 3D visualizable medical data with the medical scene being visualized for the operator. Various techniques for registering the visualizable medical data with the medical scene may be used, including matching features in 3D space with features in the visualizable medical data known to be in the medical scene, such as tumors, bones, blood vessels, etc. Manual registration may also be possible where an operator or other technician manipulates the pose of the visualizable medical data relative to the scene.

In block 320, changing pose information is determined for a medical device. The medical device for which pose information is determined in block 320 may be different from a medical device used for visualization of data in block 310.

Returning again to block 320, pose information for the medical device may be determined using any system, device, method, or technique such as the tracking systems described herein. For example, if the medical device is an ablation needle, such as ablation needle 245 in FIGS. 2A and 2B, then determining the pose information for the ablation needle 245 may include receiving tracking information from one or more position sensors sensing the position of ablation needle 245.

As depicted in FIGS. 6A-6C, pose information for the medical device may be determined in other ways as well. For example, as shown in FIG. 6A, a display 621 may have a touchscreen that allows an operator to use her finger 645 as the medical device 645 to indicate the location of an annotation. The visualizable medical data 656 may be shown on display 621. As the operator moves her finger 645, an annotation may appear on display 621 (not pictured in FIG. 6A) or on a separate display of the image 656, as depicted in FIG. 6C. In FIG. 6C, we see an annotation 671 that has been drawn by an operator up to point 680. This annotation 671 is positioned on image 656 and both are displayed on display 620. An operator may have dual displays 621 and 620 and be able to see both simultaneously.

The medical device 645 used to point to an object on a screen may also be a stylus, needle, or any other appropriate medical device 645. Further, in some embodiments, the device used for input may not be a screen 621, but may instead be a drawing tablet, or other input device (in which case image 656 may or may not be displayed on the device).

In some embodiments, a medical device, such as finger 645 in FIG. 6B, may be used to point at an image 656 displayed on a display 622. An operator may be able to point medical device 645 at the image 656 in order to define an annotation 671 up to a point 680. Pointing with medical device 645 at display 622 may define an intersection between medical device 645 and image 656. That intersection may define the point 680 that is used to define or generate the annotation 671. The medical device 645 used to point at the screen may also be a remote (such as a Nintendo Wii controller), a surgical instrument, such as an ablation needle or scalpel, eye gaze or head direction, or any other appropriate medical device.

Returning again to FIG. 3 and block 320, as pose information changes over time (e.g., because the medical device is being moved), such as described above with respect to FIGS. 1A-1D, the changing pose information for the medical device over time is determined. In one embodiment, changing pose information is collected before proceeding to block 330. In another embodiment, the changing pose information for the medical device is collected iteratively and blocks 330-350 are performed as part of those iterations. Further, in some embodiments, pose information for the visualizable medical data, changing pose information for the medical device, and the other blocks are performed iteratively. In yet other embodiments, pose information in block 310 for the visualizable medical data and changing pose information for the medical device in block 320 are updated within the system as the updated pose information is received and this latest pose information is used in subsequent blocks 330-350.

In block 330, annotations are generated in 3D space based on the pose information received in blocks 310 and 320. That is, the pose for the visualizable medical data (block 310) and the pose for the medical device (block 320) may be used to determine the annotations in 3D space (block 330). Referring again to FIGS. 1A-1D, needle 145 and or image 156 may have their poses change over time. The needle 145 and the image 156 may together define a point or mark 180 that changes over time as the poses of device 145 and image 156 change. That is, if point 180 is defined by an axis extending out of the tip of needle 145 and its intersection with the plane of the image 156, then as the needle 145 moves and/or the image 156 moves, the point 180 will change. As point 180 changes over time, it defines a curve, spline, segmented line, or other annotation that the operator is making. The annotations defined by these one or more movements is shown in FIG. 1B as annotation 171.

Figure 4:
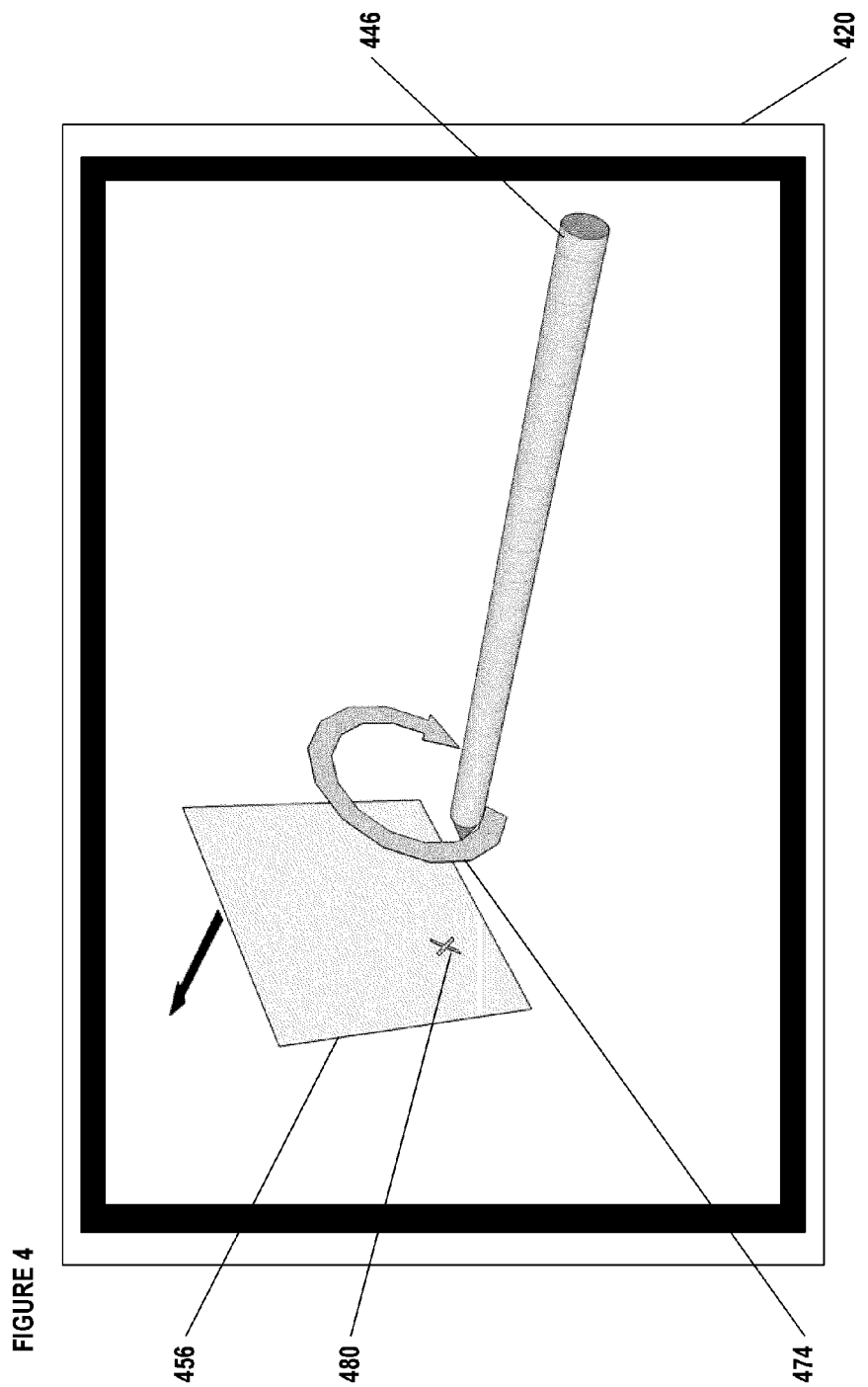
FIG. 4 illustrates a fifth example interface for image annotation in image-guided medical procedures.
Figure 5:
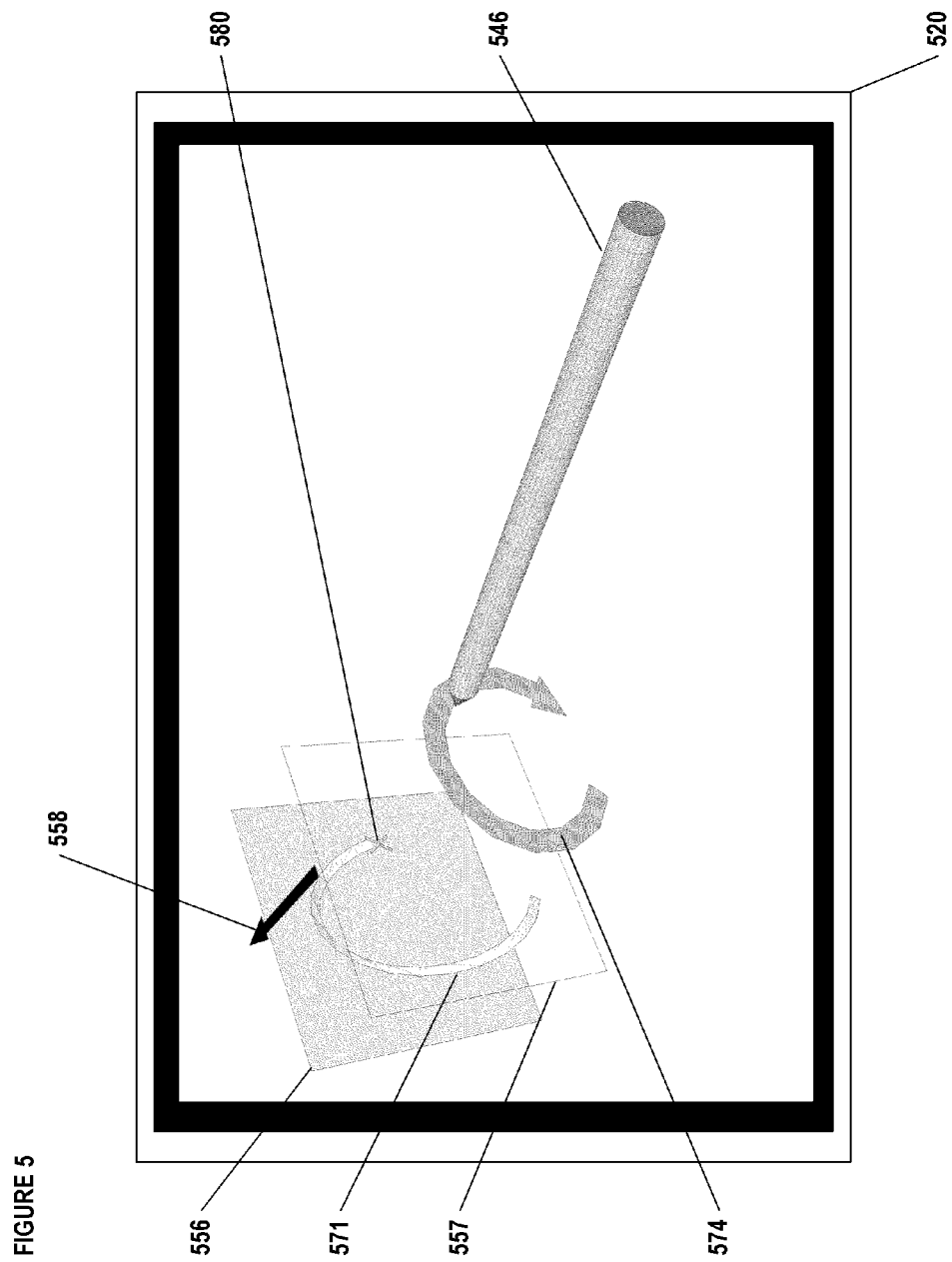
FIG. 5 illustrates a sixth example interface for image annotation in image-guided medical procedures.

FIG. 4 depicts a medical device 446 and an image 456 that together define an intersection point 480. The curve 474 shows a motion that an operator is going to make (curve 474 may or may not be displayed on display 420). As depicted in FIG. 5, after the operator has moved the medical device 546 through part of the desired curve of movement 574, an annotation 571 is created by the movement of intersection point 580. In this case, both device 546 and image 556 have been moved so annotation 571 is not planar. Instead, annotation 571 is a three-dimensional surface. The movement of image 556 is also illustrated by the outline 557 of the image's original placement at the start of the annotation (outline 557 may or may not be displayed on display 520)—and by arrow 558. As discussed briefly above, the annotation determined may be a spline, a series of lines, a series of triangles, a point cloud, a series of voxels, or any other appropriate representation in 3D space. The generated annotation may also be termed or thought of as "virtual ink." In some embodiments, the annotation may be termed "virtual ink" when it corresponds to the drawing of ink on the image plane as the drawing instrument and image plane move.

After an annotation has been created in 3D space in block 330 then in block 340 image guidance information is generated based on the annotation. Generating image guidance information based on the annotation in block 330 may include generating a 3D model or series of 3D models that represent the medical scene to be displayed to the operator. For example, as depicted in FIG. 1D, after a first annotation 171/173 is defined and a second annotation 172 is defined, generating image guidance data may include registering in the same 3D space, or determining transformations among, the various annotations 171-173 and the image 156. If the image 156 is, for example, a planar representation of 3D visualizable medical data, such as a CT scan, then determining the guidance information in block 340 may include incorporating a planar slice of the CT data corresponding to the image 156. Further, determining image guidance information may include numerous other techniques, methods, and systems, such as those described in Image Management in Image-Guided Medical Procedures, to Sharif Razzaque et al., filed concurrently herewith, which is incorporated by reference above for all purposes.

After image guidance information has been generated based on the annotation in block 340, a graphical rendering of the image guidance information is displayed in block 350. In some embodiments, the display of graphical information can be monoscopic or stereoscopic. Further, multiple rendering techniques may be used. Edges or areas near the edge of a region of interest defined by the annotation, a medical device, or the image, may be displayed in a blurred or fading manner. Objects near objects of interest such as the image, the annotation, or the medical device may be displayed in sharper focus, may be displayed brighter, etc. In one embodiment, if an additional set of 3D visualizable medical data is displayed, a tunnel or cut-through that set of medical data may be made so that an image can be shown. Consider for example, FIG. 6B. If another set of 3D data is being displayed on display 622 (not depicted in FIG. 6B), then the additional data may have a cut-through so that image 656 can be seen and the areas surrounding image 656 on display 622 may show the additional visualizable medical data. Turning to FIG. 1B, it is possible that medical device 145 and/or image 156 may define a region of interest and items in that region of interest may be displayed distinctly from the rest of the data displayed on screen 120. For example, if additional medical data is being displayed, then data from that additional medical display may be displayed within a region of interest around image 156 and/or medical device 145.

Figure 7B:
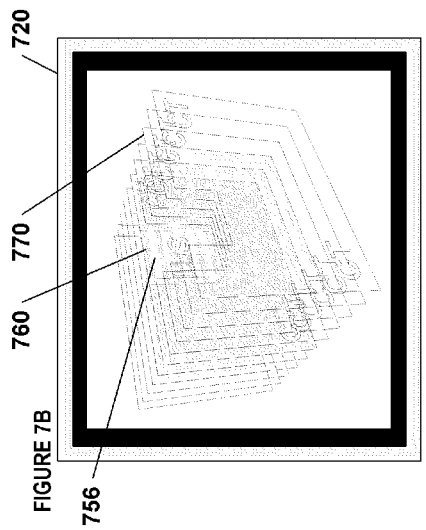
FIGS. 7A-7D illustrates a tenth example interface for image annotation in image-guided medical procedures.
Figure 7D:
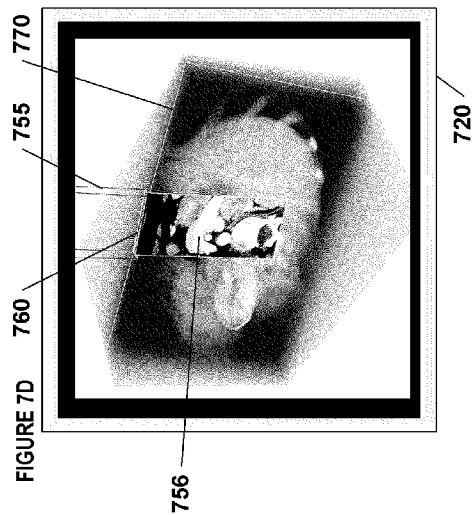
Figure 7A:
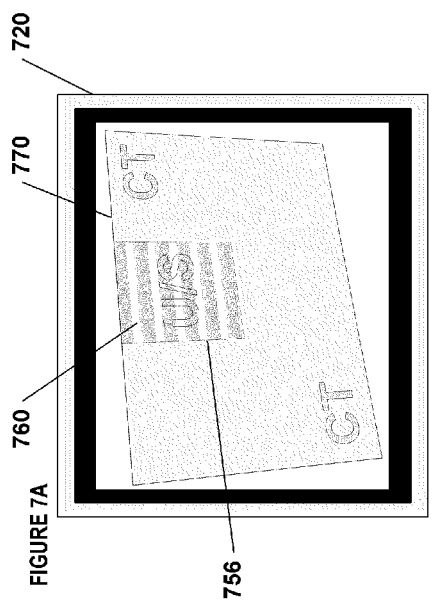
Figure 7C:
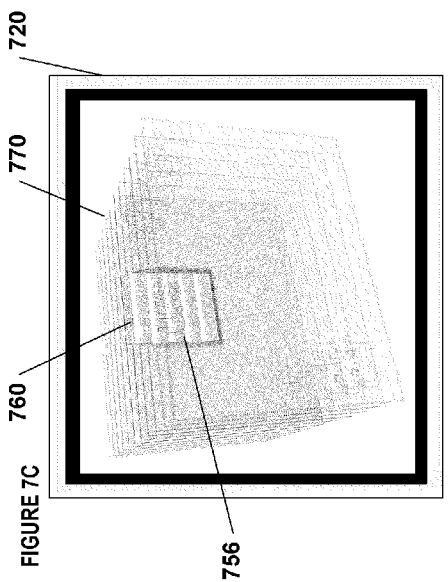

Turning to FIG. 7A, in some embodiments, a medical device may define a region of interest 760 in which an ultrasound image 756 may be shown in focus. Outside the region of interest 760, the CT scan 770 may be displayed. As depicted in FIG. 7A, a single slice of CT data 770 may be displayed outside the region of interest 760, or, as depicted in FIG. 7B, multiple slices of CT data 770 may be displayed outside the region of interest. Further, as depicted in FIG. 7C, the slices of CT data may be rendered differently depending on the distance from the region of interest. For example, planes of CT scan data 770 may be rendered more transparently (less brightly, etc) the further each is from the plane containing the region of interest. The slices of CT data may be the slices from the underlying CT data, or the slices may be generated to be, e.g., parallel or nearly parallel, with a plane associated with the region of interest 760. FIG. 7C also depicts that a tunnel may be cut through the rendered slices of the CT scan 770 in order to display the region of interest 760 without or with little overlap. This tunnel may be altered as the region of interest or CT scan data are moved to always allow the operator to view the region of interest. FIG. 7D depicts a semi-realistic rendering of a CT scan 770 around a region of interest 760. Inside the region of interest 760, an ultrasound image 756 is displayed. Also displayed on display 720 in FIG. 7D, is an outline of the medical device 755.

As noted extensively herein, the data shown in the region of interest may be any appropriate visualizable medical data, not limited to ultrasound or CT data. Further, the data displayed outside of the region of interest may be any visualizable medical data, and may even be from the same data set as the data shown in the region of interest. For example, MRI data may be shown in fading planes outside of the region of interest and in focus (and visualizable through a tunnel) inside the region of interest. Further, annotation may be displayed along with the rendering of the visualizable medical data inside and/or outside of the region of interest. In this manner, an operator may see the annotations in the context of the visualizable medical data.

In rendering the annotation, each point of the line segment, spline segment, point cloud, etc. may be made transparent and/or blurry based on its distance from the region of interest, and its rendering may be controlled using various graphic techniques, such as bit maps and pixel shaders, such as those discussed in Image Management in Image-Guided Medical Procedures, to Sharif Razzaque et al., filed concurrently herewith, which is incorporated by reference above for all purposes.

The blocks of process 300 may be performed in a different order, may be augmented by other blocks or may have subblocks within the blocks shown. Further, the process 300 may be performed on a single computer or processor, on multiple computers or processors, on a single or multiple virtual machines, and/or in a distributed fashion on multiple processors, devices, machines, or virtual machines.

Example Procedure

Consider an example ablation procedure. Lesions, which are often less than 3 cm in width, are typical targets of ablation. A physician may be able to see the lesions in a CT scan more clearly than she can in an ultrasound image. The physician may mark the lesions with annotations by navigating around the CT scan data using the techniques herein and various techniques in Image Management in Image-Guided Medical Procedures, to Sharif Razzaque et al., filed concurrently herewith, which is incorporated by reference above for all purposes.

That is, the physician may manipulate a medical device, such as an ultrasound transducer, in order to navigate and view CT data preoperatively (or intraoperatively). The physician may be able to see the small lesions in the CT data. The physician can then annotate those lesions, perhaps by circling, creating a sphere around them, and/or drawing an arrow pointing to them, using annotation the techniques herein.

Intraoperatively, the physician may be able to leverage the preoperative lesion annotation. The physician may use intraoperative ultrasound in order to spot the current location of the various lesions, guided at least in part by the annotation made in 3D space relative to the CT scan. By doing this, the physician has utilized both the relative ease of discovery of lesions on the CT scan as well as the intraoperative accuracy of locating the lesions in the ultrasound. This can increase accuracy and reduce operative times and the problems and costs associated therewith.

Although an example of an ablation is given, these techniques may be used with numerous other procedures, such as laparoscopic, endoscopic, arthroscopic, robotic and percutaneous procedures, resections, tissue transplantation, training, diagnostic, as well as drug delivery procedures, etc.

Other Embodiments

The processes, computer readable medium, and systems described herein may be performed on various types of hardware, such as computer systems or computing devices. In some embodiments, position sensing units 210 and 240, display unit 220, image guidance unit 230, and/or any other module or unit of embodiments herein may each be separate computing devices, applications, or processes or may run as part of the same computing devices, applications, or processes—or one of more may be combined to run as part of one application or process—and/or each or one or more may be part of or run on a computing device. Computing devices or computer systems may include a bus or other communication mechanism for communicating information, and a processor coupled with the bus for processing information. A computer system or device may have a main memory, such as a random access memory or other dynamic storage device, coupled to the bus. The main memory may be used to store instructions and temporary variables. The computer system or device may also include a read-only memory or other static storage device coupled to the bus for storing static information and instructions. The computer systems or devices may also be coupled to a display, such as a CRT, LCD monitor, LED array, e-paper, projector, or stereoscopic display. Input devices may also be coupled to the computer system or device. These input devices may include a mouse, a trackball, touchscreen, tablet, foot pedal, or cursor direction keys. Computer systems or devices described herein may include the image guidance unit 230, first and second position sensing units 210 and 240, and imaging unit 250.

Each computer system or computing device may be implemented using one or more physical computers, processors, embedded devices, field programmable gate arrays (FPGAs), or computer systems or portions thereof. The instructions executed by the computer system or computing device may also be read in from a computer-readable medium. The computer-readable medium may be non-transitory, such as a CD, DVD, optical or magnetic disk, laserdisc, flash memory, or any other medium that is readable by the computer system or device. In some embodiments, hardwired circuitry may be used in place of or in combination with software instructions executed by the processor. Communication among modules, systems, devices, and elements may be over a direct or switched connections, and wired or wireless networks or connections, via directly connected wires, or any other appropriate communication mechanism. Transmission of information may be performed on the hardware layer using any appropriate system, device, or protocol, including those related to or utilizing Firewire, PCI, PCI express, CardBus, USB, CAN, SCSI, IDA, RS232, RS422, RS485, 802.11, etc. The communication among modules, systems, devices, and elements may include handshaking, notifications, coordination, encapsulation, encryption, headers, such as routing or error detecting headers, or any other appropriate communication protocol or attribute. Communication may also messages related to HTTP, HTTPS, FTP, TCP, IP, ebMS OASIS/ebXML, DICOM, DICOS, secure sockets, VPN, encrypted or unencrypted pipes, MIME, SMTP, MIME Multipart/Related Content-type, SQL, etc.

Any appropriate 3D graphics processing may be used for displaying or rendering, including processing based on OpenGL, Direct3D, Java 3D, etc. Whole, partial, or modified 3D graphics packages may also be used, such packages including 3DS Max, SolidWorks, Maya, Form Z, Cybermotion 3D, VTK, Slicer, Blender or any others. In some embodiments, various parts of the needed rendering may occur on traditional or specialized graphics hardware. The rendering may also occur on the general CPU, on programmable hardware, on a separate processor, be distributed over multiple processors, over multiple dedicated graphics cards, or using any other appropriate combination of hardware or technique.

The features and attributes of the specific embodiments disclosed above may be combined in different ways to form additional embodiments, all of which fall within the scope of the present disclosure.

Conditional language used herein, such as, among others, "can," "could," "might," "may," "e.g.," and the like, unless specifically stated otherwise, or otherwise understood within the context as used, is generally intended to convey that certain embodiments include, while other embodiments do not include, certain features, elements and/or states. Thus, such conditional language is not generally intended to imply that features, elements and/or states are in any way required for one or more embodiments or that one or more embodiments necessarily include logic for deciding, with or without author input or prompting, whether these features, elements and/or states are included or are to be performed in any particular embodiment.

Any process descriptions, elements, or blocks in the processes, methods, and flow diagrams described herein and/or depicted in the attached figures should be understood as potentially representing modules, segments, or portions of code which include one or more executable instructions for implementing specific logical functions or steps in the process. Alternate implementations are included within the scope of the embodiments described herein in which elements or functions may be deleted, executed out of order from that shown or discussed, including substantially concurrently or in reverse order, depending on the functionality involved, as would be understood by those skilled in the art.

All of the methods and processes described above may be embodied in, and fully automated via, software code modules executed by one or more general purpose computers or processors, such as those computer systems described above. The code modules may be stored in any type of computer-readable medium or other computer storage device. Some or all of the methods may alternatively be embodied in specialized computer hardware.

It should be emphasized that many variations and modifications may be made to the above-described embodiments, the elements of which are to be understood as being among other acceptable examples. All such modifications and variations are intended to be included herein within the scope of this disclosure and protected by the following claims.

What is claimed is:

1. A method for image annotation in image guided medical procedures, comprising:
    determining, with one or more computing devices, position and orientation of a first medical device;
    determining position and orientation of an imaging area based at least on the position and orientation of the first medical device;

causing one or more displays to display a perspective view of an image corresponding to the imaging area within a virtual 3D space based at least on the position and orientation of the first medical device relative to a position of a user;

tracking, with the one or more computing devices, a position of a second medical device; and causing the one or more displays to display an annotation in the virtual 3D space based at least in part on an intersection of an axis of the second medical device with the imaging area.

2. The method of claim 1, wherein the second medical device comprises at least one of a needle, a stylus, an ultrasound transducer, a cauterizer, a scalpel, and a glove.

3. The method of claim 1, wherein causing the one or more displays to display the annotation comprises causing the one or more displays to display the annotation based at least on the intersection of the at least a portion of the second medical device with the imaging area over time.

4. The method of claim 1, wherein the position of the user comprises a predetermined location.

5. A system for image annotation in image-guided medical procedures, comprising:

one or more computing devices in communication with one or more displays, a first medical device, and a second medical device, wherein the one or more computing devices are configured to:

determine position and orientation of the first medical device;

determine position and orientation of an imaging area based at least on the position and orientation of the first medical device;

cause the one or more displays to display a perspective view of an image corresponding to the imaging area within a virtual 3D space based at least on the position and orientation of the first medical device relative to a position of a user;

track a position of the second medical device; and cause the one or more displays to display an annotation in the virtual 3D space based at least on an intersection of an axis of the second medical device with the imaging area.

6. The system of claim 5, wherein the intersection comprises contact between the at least a portion of the second medical device and the one or more displays.

7. The system of claim 5, wherein the second medical device comprises at least one of a needle, a stylus, an ultrasound transducer, a cauterizer, or a scalpel.

8. The system of claim 5, wherein the second medical device comprises a glove.

9. The system of claim 5, wherein the one or more computing devices are further configured to cause the one or more displays to display virtual ink at the intersection of the at least a portion of the second medical device and the perspective view of the imaging area.

10. The system of claim 5, wherein to cause the one or more displays to display the annotation, the one or more computing devices are configured to cause the one or more displays to display the annotation based at least on the intersection of the at least a portion of the second medical device with the imaging area over time.

11. The system of claim 5, wherein to track the position of the second medical device the one or more computing devices are configured to receive input from a touch screen and determine position based on the input from the touch screen.

12. The system of claim 5, wherein to track position of the second medical device the one or more computing devices are configured to receive input from a remote pointer and determine position based on the input from the remote pointer.

13. The system of claim 5, wherein the position of the user comprises a predetermined location.

14. A non-transient computer-readable medium comprising computer-executable instructions, said computer-executable instructions, when executing on one or more computing devices, cause the one or more computing devices to:

determine position and orientation of a first medical device;

determine position and orientation of an imaging area based at least on the position and orientation of the first medical device;

cause one or more displays to display a perspective view of an image corresponding to the imaging area within a virtual 3D space based at least on the position and orientation of the first medical device relative to a position of a user;

track a position of a second medical device; and cause the one or more displays to display an annotation in the virtual 3D space based at least on an intersection of an axis of the second medical device with the imaging area.

15. The non-transient computer-readable medium of claim 14, wherein causing the one or more displays to display the annotation comprises causing the one or more displays to display the annotation based at least on the intersection of the at least a portion of the second medical device with the imaging area over time.

16. The non-transient computer-readable medium of claim 14, wherein the position of the user comprises a predetermined location.

* * * * *

UNITED STATES PATENT AND TRADEMARK OFFICE
CERTIFICATE OF CORRECTION

Page 1 of 1

PATENT NO. : 9,107,698 B2
APPLICATION NO. : 14/047628
DATED : August 18, 2015
INVENTOR(S) : Sharif Razzaque It is certified that error appears in the above-identified patent and that said Letters Patent is hereby corrected as shown below:

Specification

In column 6 at line 12, Change "meaning" to --meaning.--.

In column 10 at lines 17-18, Change "independent f's" to --independent of f's--.

Signed and Sealed this
Twenty-fourth Day of May, 2016

Michelle K. Lee
*Director of the United States Patent and Trademark Office*